(12) United States Patent
Eidam et al.

(10) Patent No.: US 11,341,223 B1
(45) Date of Patent: *May 24, 2022

(54) WEARABLE COMPUTING DEVICE SECURE ACCESS BADGE

(71) Applicant: Wells Fargo Bank, N.A., San Francisco, CA (US)

(72) Inventors: Kourtney Eidam, Marietta, GA (US); Andrew J. Garner, IV, State Road, NC (US); Dennis Montenegro, Concord, CA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 16/704,872

(22) Filed: Dec. 5, 2019

Related U.S. Application Data

(63) Continuation of application No. 15/394,597, filed on Dec. 29, 2016, now Pat. No. 10,546,108.

(51) Int. Cl.
*G06F 21/32* (2013.01)
*A61B 5/117* (2016.01)
(Continued)

(52) U.S. Cl.
CPC ............ *G06F 21/32* (2013.01); *A61B 5/0015* (2013.01); *A61B 5/117* (2013.01); *A61B 5/6802* (2013.01);
(Continued)

(58) Field of Classification Search
CPC ..... A61B 5/0015; A61B 5/117; A61B 5/6802; G06F 21/32; G06F 21/35;
(Continued)

(56) References Cited

U.S. PATENT DOCUMENTS

| 7,258,272 B2 | 8/2007 | Yoshizane et al. |
| 7,681,232 B2 | 3/2010 | Nordentoft et al. |

(Continued)

FOREIGN PATENT DOCUMENTS

| EP | 1326196 A1 | 9/2003 |
| EP | 1775674 A1 | 4/2007 |

OTHER PUBLICATIONS

U.S. Appl. No. 15/394,581, by Kourtney Eidam, filed Dec. 29, 2016.
(Continued)

*Primary Examiner* — Theodore C Parsons
(74) *Attorney, Agent, or Firm* — Shumaker & Sieffert, P.A.

(57) ABSTRACT

Techniques are described for enabling a user to access a secure system based on vital signs of the user that are collected by a wearable device worn by the user. The vital signs of the user may be used as an extra level of security when accessing the secure system. For example, a computing device may automatically validate that a user requesting access to a secure system is a person and not a robot based on receipt of vital signs of the user. As another example, a computing device may operate as a secure access badge that first analyzes vital signs of a user to confirm that the user is not in distress before sending an access signal to gain access to a secure system. In either example, the computing device may be a wearable device, or be paired to a wearable device to receive the vital signs.

20 Claims, 7 Drawing Sheets

(51) Int. Cl.
| | |
|---|---|
| *H04L 29/06* | (2006.01) |
| *H04W 12/06* | (2021.01) |
| *A61B 5/00* | (2006.01) |
| *G06F 21/35* | (2013.01) |

(52) U.S. Cl.
CPC .......... *G06F 21/35* (2013.01); *H04L 63/0853* (2013.01); *H04L 63/0861* (2013.01); *H04L 63/102* (2013.01); *H04L 63/107* (2013.01); *H04W 12/06* (2013.01); *G06F 2221/2133* (2013.01); *G06F 2221/2139* (2013.01)

(58) Field of Classification Search
CPC ..... G06F 2221/2133; G06F 2221/2139; H04L 63/0853; H04L 63/0861; H04L 63/102; H04L 63/107; H04W 12/06; H04W 12/50; H04W 12/63
See application file for complete search history.

(56) References Cited

U.S. PATENT DOCUMENTS

| | | | |
|---|---|---|---|
| 8,276,816 | B2 | 10/2012 | Gardner |
| 8,417,584 | B2 | 4/2013 | Ross |
| 8,715,178 | B2 | 5/2014 | Price et al. |
| 8,715,179 | B2 | 5/2014 | Price et al. |
| 9,124,570 | B1 | 9/2015 | Asher et al. |
| 9,721,409 | B2 | 8/2017 | Sezan et al. |
| 9,743,443 | B2 * | 8/2017 | Panther ................. H04W 12/50 |
| 9,892,576 | B2 | 2/2018 | Kursun et al. |
| 9,985,943 | B1 | 5/2018 | Reading et al. |
| 10,133,979 | B1 | 11/2018 | Eidam et al. |
| 10,318,860 | B1 | 7/2019 | Eidam et al. |
| 10,546,108 | B1 | 1/2020 | Eidam et al. |
| 2004/0019570 | A1 | 1/2004 | Bolle et al. |
| 2007/0252001 | A1 | 11/2007 | Kail et al. |
| 2009/0328163 | A1 | 12/2009 | Preece |
| 2011/0201960 | A1 | 8/2011 | Price et al. |
| 2014/0188770 | A1 * | 7/2014 | Agrafioti ............... A61B 5/7267 706/13 |
| 2014/0189807 | A1 | 7/2014 | Cahill et al. |
| 2015/0235055 | A1 | 8/2015 | An et al. |
| 2015/0288681 | A1 | 10/2015 | Park et al. |
| 2016/0112415 | A1 | 4/2016 | Park et al. |
| 2016/0135046 | A1 | 5/2016 | John Archibald et al. |
| 2016/0378964 | A1 | 12/2016 | Singh et al. |
| 2017/0083909 | A1 | 3/2017 | Mork et al. |
| 2017/0180348 | A1 | 6/2017 | Piccolotto et al. |
| 2018/0034859 | A1 * | 2/2018 | Aronowitz ............ H04L 63/205 |
| 2018/0069847 | A1 | 3/2018 | Portnuru et al. |
| 2018/0150126 | A1 | 5/2018 | Xu et al. |
| 2018/0302416 | A1 * | 10/2018 | Einberg ............. H04L 63/0861 |

OTHER PUBLICATIONS

Ahlberg, "Smart Skin: Electronics that stick and stretch like a temporary tattoo," Illinois News Bureau, accessed from https://news_illinois.edu/blog/view/6367/205260, Aug. 11, 2011, 5 pp.
Boden, "Developers unveil electronic tattoos for payment and healthcare," NFC World Knowledge Centre accessed from https://www.nfcworld.com/2015/12/01/340243/developers-unveil-electronic-tattoos-payments-healthcare/, Dec. 1, 2015, 3 pp.
McClay et al., "A Real-Time Magnetoencephalography Brain-Computer Interface Using Interactive 3D Visualization and the Hadoop Ecosystem," Brain Science., Sep. 30, 2015, 5, 419-440. 22 pp.
McClay et al., "Amplitude-modulated phase-only filtering and high-dimensional warping for registration on MRI brain images", Proceeding of SPIE Digital Library, Sep. 8, 2006, 15 pp.
Reutzel., "PayThink The Dawn of the Payment Tattoo," Payments-Source, accessed from https://www.paymentssource.com/opinion/the-dawn-of-the-payment-tattoo, Jul. 29, 2014, 5 pp.
Suzuki et al., "Ishin-Den-Shin: Transmitting Sound Through Touch," accessed from https://www.disneyresearch.com/project/ishindenshin/ on Dec. 2, 2016, 5 pp.
United States, Government Accountability Office, Facial Recognition Technology: Commercial Users, Privacy Issues, and Applicable Federal Law, Jul. 2015, 54 pp.
Prosecution History from U.S. Appl. No. 15/394,581 dated Jun. 15, 2018 through Jan. 13, 2020, 212 pp.
Prosecution History from U.S. Appl. No. 15/394,597, dated Oct. 29, 2018 through Dec. 30, 2019, 113 pp.
Response to Office Action dated Jun. 25, 2020, from U.S. Appl. No. 15/394,581, filed Sep. 25, 2020, 13 pp.
Office Action from U.S. Appl. No. 15/394,581, dated Jun. 25, 2020, 23 pp.
Final Office Action from U.S. Appl. No. 15/394,581, dated Dec. 1, 2020, 23 pp.
Office Action from U.S. Appl. No. 15/394,581, dated Jul. 6, 2021, 23 pp.
Response to Final Office Action dated Dec. 1, 2020 and the Advisory Action dated Feb. 19, 2020, from U.S. Appl. No. 15/394,581, filed Mar. 25, 2021, 11 pp.
Advisory Action from U.S. Appl. No. 15/394,581, dated Feb. 19, 2021, 3 pp.
Response to Final Office Action dated Dec. 1, 2020 from U.S. Appl. No. 15/394,581, filed Jan. 29, 2021, 6 pp.
Advisory Action from U.S. Appl. No. 15/394,581, dated Apr. 27, 2021, 3 pp.
Final Office Action from U.S. Appl. No. 15/394,581, dated Dec. 15, 2021, 26 pp.

* cited by examiner

WEARABLE COMPUTING DEVICE SECURE ACCESS BADGE

CROSS REFERENCE

This application is a continuation of U.S. patent application Ser. No. 15/394,597 filed on Dec. 29, 2016, the content of which is hereby incorporated by reference in its entirety.

TECHNICAL FIELD

The disclosure relates to wearable technology.

BACKGROUND

Wearable computing devices may comprise any of a wide range of computing devices that are configured to be attached to some portion of a user's body. In some examples, a wearable device may comprise a computing device in the form of a watch, a bracelet, an arm band, an ankle band, an ear cuff, or another form factor capable of being worn by encircling or otherwise attaching to some portion of the user's body. In other examples, a wearable device may comprise electronic skin technology, also referred to as "skin tech" or "digital tattoo," in the form of a thin, flexible film that includes embedded electronics capable of being worn by adhering directly to a user's skin, e.g., as a sticker, patch, or temporary tattoo.

Wearable devices may include sensors with conducting elements that are in contact with a portion of a user's body to monitor one or more of the user's vital signs, e.g., heart rate, breathing rate, blood pressure, and/or body temperature. Wearable devices may also, or alternatively, include sensors such as pedometers, accelerometers, microphones, cameras, or the like, to monitor the user's behavioral biometrics, e.g., gait, voice, or speed of typing, talking or texting. Typically, a wearable device includes simple circuitry capable of collecting the vital signs and/or behavioral biometrics, but is linked or paired to another computing device capable of storing, analyzing, outputting, and communicating the collected vital signs and/or behavioral biometrics of the user. In one example, the computing device may comprise a smart phone executing a health or fitness application that receives vital signs of a user from a paired wearable device that is worn by the user.

SUMMARY

In general, this disclosure describes techniques for enabling a user to access a secure system using a wearable device worn by the user. According to the disclosed techniques, vital signs and/or behavioral biometrics of the user that are collected by the wearable device may be used as an extra level of security when the user is accessing the secure system. For example, a computing device may automatically validate that a user requesting access to a secure system is a person and not a robot based on receipt of vital signs of the user. As another example, a computing device may operate as a secure access badge that first analyzes vital signs of a user to confirm that the user is not in distress before sending an access signal to gain access to a secure system. In either example, the computing device may either be a wearable device itself, or be paired to a wearable device to receive the vital signs.

In one example, this disclosure is directed to a computing device comprising a memory configured to store at least one user profile for a user of the computing device, and one or more processors in communication with the memory. The one or more processors are configured to request access to a secure system in response to user input from the user; in response to the request, receive, from the secure system, a prompt to validate the user as a person; receive one or more vital signs of the user; and based on the receipt of the one or more vital signs of the user, automatically validate the user as a person to the secure system.

In another example, this disclosure is directed to a method comprising requesting, by a computing device, access to a secure system in response to user input from a user of the computing device; receiving, by the computing device and from the secure system, a prompt to validate the user as a person; receiving, by the computing device, one or more vital signs of the user; and based on the receipt of the one or more vital signs of the user, automatically validating, by the computing device, the user as a person to the secure system.

In a further example, this disclosure is directed to a non-transitory computer readable storage medium storing instructions that when executed cause one or more processors of a computing device to request access to a secure system in response to user input from a user of the computing device; receive, from the secure system, a prompt to validate the user as a person; receive one or more vital signs of the user; and based on the receipt of the vital signs of the user, automatically validate the user as a person to the secure system.

In one example, this disclosure is directed to a computing device comprising a memory configured to store at least one user profile for a user of the computing device, and one or more processors in communication with the memory. The one or more processors are configured to establish communication with an access terminal for a secure system; receive one or more vital signs of the user; compare the one or more vital signs of the user against the at least one user profile for the user; and based on the one or more vital signs substantially matching the at least one user profile, send, to the access terminal, an access signal requesting access to the secure system for the user.

In another example, this disclosure is directed to a method comprising establishing, by a computing device, communication with an access terminal for a secure system; receiving, by the computing device, one or more vital signs of a user of the computing device; comparing, by the computing device, the one or more vital signs of the user against at least one user profile for the user stored by the computing device; and based on the one or more vital signs substantially matching the at least one user profile, sending, by the computing device and to the access terminal, an access signal requesting access to the secure system for the user.

In a further example, this disclosure is directed to an access terminal for a secure system, the access terminal comprising a memory configured to store a database of authorized users of the secure system; and one or more processors in communication with the memory. The one or more processors are configured to receive an access signal from a computing device requesting access to the secure system for a user of the computing device; receive one or more vital signs of the user from the computing device; authenticate the user based on the access signal; compare the one or more vital signs of the user against a user profile for the authenticated user included in the database; and based on the one or more vital signs substantially matching the user profile, grant access to the secure system for the authenticated user.

In an additional example, this disclosure is directed to, method comprising receiving, by an access terminal for a secure system and from a computing device, an access signal requesting access to the secure system for a user of the computing device; receiving, by the access terminal and from the computing device, one or more vital signs of the user; authenticating, by the access terminal, the user based on the access signal; comparing, by the access terminal, the one or more vital signs of the user against a user profile for the authenticated user stored by the access terminal; and based on the one or more vital signs substantially matching the user profile, granting access to the secure system for the authenticated user.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
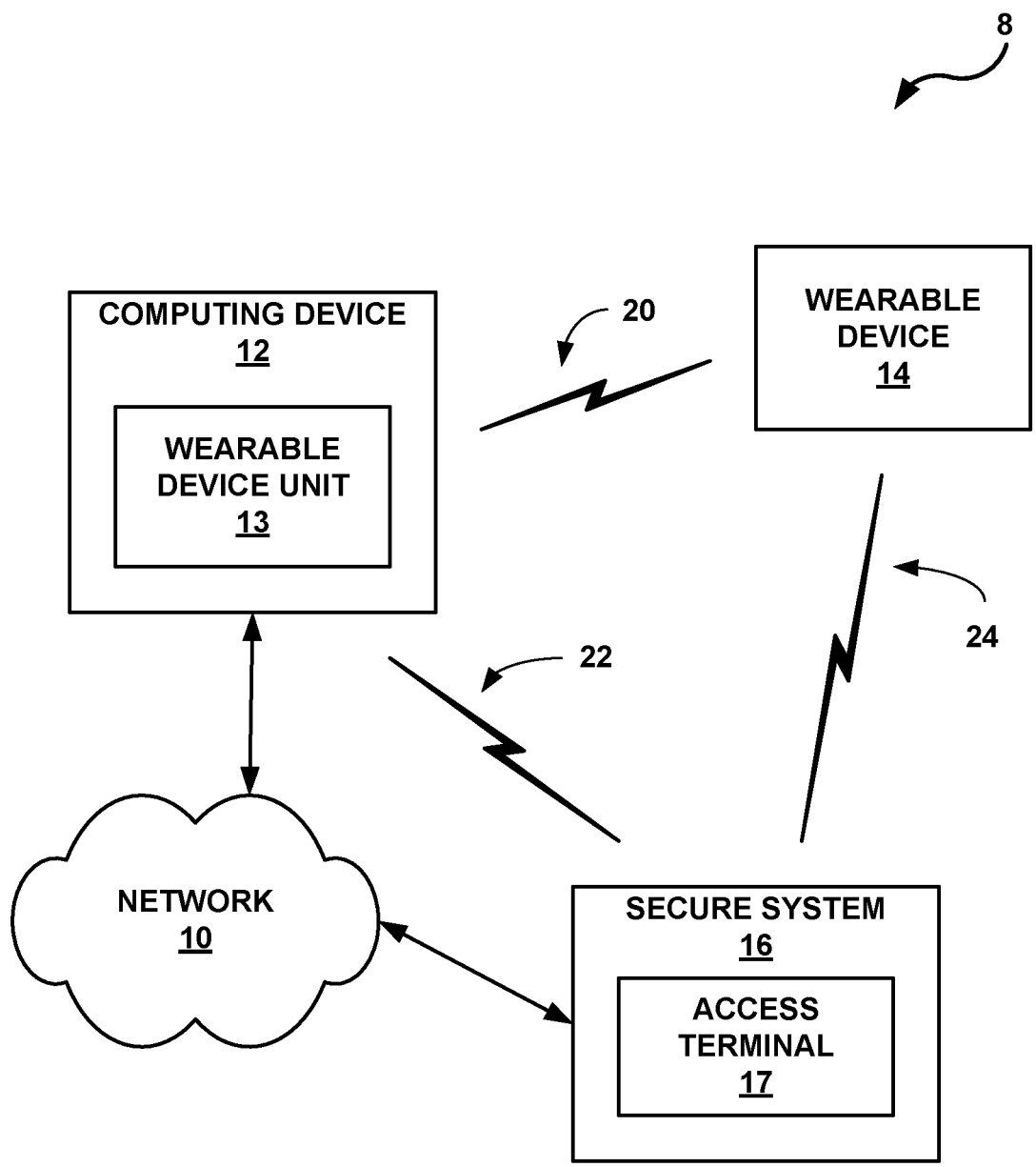
FIG. 1 is a block diagram illustrating an example network system including a wearable computing device configured to enable user access to a secure system, in accordance with the techniques of this disclosure.

FIG. 1 is a block diagram illustrating an example network system 8 including a wearable computing device 14 configured to enable user access to a secure system 16, in accordance with the techniques of this disclosure. As illustrated in FIG. 1, network system 8 includes a computing device 12 that is in communication with wearable device 14 via a wireless signal 20 and in communication with secure system 16 via a network 10 or a wireless signal 22. In some examples, wearable device 14 may also be in direct communication with secure system 16 via a wireless signal 24 or via a network, e.g., network 10 or another network not shown in FIG. 1.

According to the techniques described in this disclosure, wearable device 14 collects or monitors vital signs and/or behavioral biometrics of a user that is wearing the wearable device 14, and the collected vital signs and/or behavioral biometrics are then used as an extra level of security when the user is accessing secure system 17. In one example of the disclosed techniques, computing device 12 may automatically, i.e., without manual input from a user, validate that the user requesting access to secure system 17 is a person and not a robot based on receipt of vital signs of the user from wearable device 14. As another example of the disclosed techniques, computing device 12 may operate as a secure access badge that first analyzes vital signs of a user received from wearable device 14 to confirm that the user is not in distress before sending an access signal to gain access to secure system 16. In other examples, wearable device 14 itself may be configured to request access to secure system 16 for a user based on the vital signs collected by wearable device 14 such that computing device 12 may not be necessary for the performance of the disclosed techniques.

Secure system 16 may be a portion of a corporation, financial institution, government agency, merchant or retailer, or other entity that requires verification or authentication of a user's identify prior to granting the user access. In some examples, secure system 16 may be a physical location such as a secure building or a secure area within a building. In other examples, secure system 16 may be a secure computing system, a secure database, a secure website, or a secure online payment portal. In the case where secure system 16 is a secure computing system, secure system 16 may be a centralized or distributed system of one or more computing devices, such as desktop computers, laptops, workstations, wireless devices, network-ready appliances, file servers, print servers, or other devices.

As shown in FIG. 1, secure system 16 is in communication with computing device 12 through network 10 or via wireless signal 22. In some examples, network 10 may comprise a private network associated with secure system 16 or the entity of which secure system 16 is a part. In other examples, network 10 may comprise a public network, such as the Internet. Although illustrated as a single entity, network 10 may comprise a combination of public and/or private networks. In some examples, network 10 may comprise one or more of a wide area network (WAN) (e.g., the Internet), a local area network (LAN), a virtual private network (VPN), or another wired or wireless communication network.

Wireless signal 22 may conform to a short-range wireless communication protocol, such as near-field communication (NFC), radio-frequency identification (RFID), Bluetooth®, or the like, that enables communication between two devices when the two devices within a certain distance from each other. As one example, NFC may enable communication between two devices that are within 20 centimeters of each other. As another example, Bluetooth may enable communication between two devices that are within 100 meters of each other. As a further example, RFID may enable communication between two devices that are within several hundred meters of each other.

In the example illustrated in FIG. 1, secure system 16 includes an access terminal 17. In one example, access terminal 17 may be a physical security checkpoint at the entrance of a secure building or a secure area within a building, or at a computer terminal used to access a secure computing system. In another example, access terminal 17 may be a virtual security checkpoint at a login to a secure computing system or a secure database within a computing system. In the example wherein access terminal 17 is a physical security checkpoint, computing device 12 may communicate with access terminal 17 via wireless signal 22 when within a certain distance. In the example where access terminal 17 is a virtual security checkpoint, computing device 12 may communicate with access terminal 17 via network 10 based on a user input request. An example of access terminal 17 is described in more detail below with respect to FIG. 4.

Computing device 12 may comprise any of a wide range of user devices, including laptop or desktop computers, tablet computers, so-called "smart" phones, "smart" pads, or other personal digital appliances equipped for wired or wireless communication. Computing device 12 may include at least one user interface device (not shown) that enables a user to interact with computing device 12. In some examples, the user interface device of computing device 12 may be configured to receive tactile, audio, or visual input. In addition to receiving input from the user, the user interface device of computing device 12 may be configured to output content such as a graphical user interface (GUI) for display, e.g., at a display device associated with computing device 12.

In the example illustrated in FIG. 1, computing device 12 communicates with secure system 16 via network 10 or wireless signal 22, and communicates with wearable device 14 via wireless signal 20. Wireless signal 20 may conform to a short-range wireless communication protocol, such as NFC or Bluetooth. In the example illustrated in FIG. 1, computing device 12 includes a wearable device unit 13. Computing device 12 may use wearable device unit 13 to pair or link with wearable device 14, e.g., to allow communication between computing device 12 and wearable device 14. For example, wearable device unit 13 may establish a pairing with wearable device 14 through an exchange of information via wireless signal 20. After the pairing is established, computing device 12 detects when wearable device 14 is proximate to paired computing device 12, and initiates a communication session with wearable device 14. An example of computing device 12 is described in more detail below with respect to FIG. 2.

Wearable device 14 may comprise any of a wide range of computing devices that are configured to be attached to some portion of a user's body. In some examples, wearable device 14 may comprise a computing device in the form of a watch, a bracelet, an arm band, an ankle band, an ear cuff, or another form factor capable of being worn by encircling some portion of the user's body. In other examples, wearable device 14 may comprise electronic skin technology, also referred to as "skin tech" or "digital tattoo," in the form of a thin, flexible film that includes embedded electronics capable of being worn by adhering directly to a user's skin, e.g., as a sticker, patch, or temporary tattoo.

Wearable device 14 may include sensors with conducting elements that are in contact with a portion of a user's body to monitor one or more of the user's vital signs, e.g., heart rate, breathing rate, blood pressure, and/or body temperature. Wearable device 14 may also, or alternatively, include sensors such as pedometers, accelerometers, microphones, cameras, or the like, to monitor the user's behavioral biometrics, e.g., gait, voice, or speed of typing, talking or texting. Although the techniques of this disclosure are primarily described with reference to a user's vital signs, the techniques may similarly be performed with respect to a user's behavioral biometrics. For purposes of this disclosure, the term "vital signs" may be interpreted as including both a user's vital signs and a user's behavioral biometrics.

In some cases, wearable device 14 includes simple circuitry capable of collecting the vital signs of the user, but may operate as an accessory that is paired or linked to computing device 12. In this case, wearable device 14 may be considered a "dumb" or non-dynamic device that does not have full communication and/or processing capabilities. For example, wearable device 14 may be used to collect the user's vital signs, and then computing device 12 may be used to store, analyze, output, and communicate the collected vital signs. In one specific example, computing device 12 may comprise a smart phone executing a health or fitness application that tracks vital signs of the user received from wearable device 14.

In accordance with the disclosed techniques, in the case of a "dumb" wearable device, computing device 12 may receive one or more vital signs of a user from wearable device 14 via wireless signal 20. Based on the received vital signs, computing device 12 may communicate with secure system 16 via network 10 or wireless signal 22 in order to enable access to secure system 16 for the user. In this case, wearable device 14 may not be capable of communicating directly with secure system 16.

In other cases, wearable device 14 may include one or more processors, rewritable memory, and power sources. In this case, wearable device 14 may be considered a "smart" or dynamic device that is capable of accessing a network, e.g., the Internet or another communication network, and executing applications or performing other processing tasks. In this example, wearable device 14 may collect the user's vital signs, and may also store, analyze, output, and communicate the collected vital signs. In one specific example, wearable device 14 may comprise a smart watch or bracelet executing a health or fitness application that tracks vital signs of the user received from the sensors of wearable device 14.

In accordance with the disclosed techniques, in the case of a "smart" wearable device, wearable device 14 may monitor one or more vital signs of a user. Based on the monitored vital signs, wearable device 14 may communicate directly with secure system 16 via wireless signal 24 or via a network (e.g., network 10 or another network not shown in FIG. 1) in order to enable access to secure system 16 for the user. Wireless signal 24 may conform to a short-range wireless communication protocol, such as NFC, RFID, or Bluetooth. In this case, computing device 12 may not be necessary for the performance of the disclosed techniques. An example of wearable device 14 is described in more detail below with respect to FIG. 3.

This disclosure describes several different techniques in which computing device 12 and/or wearable device 14 use one or more vital signs of a user to enable access to secure system 16 for the user. The different techniques may be used alone or in combination.

As a first example of the disclosed techniques, computing device 12 may execute a browser or other applications through which a user may send a request via network 10 to access secure system 16, e.g., a retailer's website used to access an online payment portal, a company's website used to access documents or other data, or a mobile banking application or a virtual wallet application used to access a user's bank. In some examples, secure system 16 may respond via network 10 with a request for validation that the user is a person and not a robot, e.g., to avoid receiving message spam and/or automated extraction of data. This validation request may be referred to as a CAPTCHA request, although a variety of other validation requests such as click through, check box, or two step authentication are also applicable.

According to the techniques of this disclosure, in response to the validation request, computing device 12 automatically, i.e., without manual input from the user, validates the user as a person (e.g., a human being) to secure system 16 based on receipt of the user's vital signs from wearable device 14. In this way, the user may not need to determine what the validation request from secure system 16 is asking, and then manually type characters or manually select an image via the user interface device of computing device 12 to respond to the validation request. The automatic user validation techniques may increase the speed at which the user can obtain access to secure system 16 via computing device 12 while still ensuring that the user is a person and not a robot. In addition, the automatic user validation techniques may reduce an amount of network traffic between computing device 12 and secure system 16 by avoiding repeated validation requests via network 10 due to incorrect manual responses, e.g., misread or mistyped characters. In other examples, wearable device 14 may communicate directly with secure system 16 via network 10, or another network not shown in FIG. 1, to automatically validate a user without need for computing device 12.

As a second example of the disclosed techniques, computing device 12 may operate as a digital or virtual secure access badge for a user of computing device 12 to gain access to secure system 16, e.g., a secure building, a secure area of a building, a secure computing system, or a secure database in a computing system. In some examples, computing device 12 may emit an access signal that is readable by access terminal 17 for secure system 16. As one example, computing device 12 may emit the access signal via wireless signal 22 when within a certain distance from a physical version of access terminal 17. As another example, computing device 12 may emit the access signal via network 10 to a virtual version of access terminal 17 based on a user input request. In some other examples, computing device 12 may present the access signal as a scannable image, e.g., a barcode or a quick response (QR) code, on a display of computing device 12 that is readable via a laser scanner at the physical version of access terminal 17.

The user of computing device 12 may be authorized and granted access to secure system 16 based on the access signal matching one of a plurality of authorized access signals stored at access terminal 17 for secure system 16. The techniques of this disclosure enable another factor to be included in the authentication of the user. According to the disclosed techniques, prior to sending the access signal to access terminal 17, computing device 12 confirms that the user is not in distress when attempting to gain access to secure system 16 by monitoring the user's vital signs received from wearable device 14. For example, a spike in one of the user's vital signs, e.g., heart rate, may indicate that the user is nervous due to performing a nefarious action within secure system 16, or is being coerced or otherwise forced to gain access to secure system 16 by a bad actor. In this example, computing device 12 does not send the access signal to access terminal 17, and may instead send an alert to a security officer or manager associated with secure system 16 to report the failed access attempt. In other examples, computing device 12 may further use the vital signs of the user received from wearable device 14 to authenticate the identity of the user prior to sending the access signal to access terminal 17.

According to the disclosed techniques, computing device 12 may provide a first level of security by analyzing the user's vital signs to determine whether any spikes or sudden changes occur, and sending the access signal to access terminal 17 for secure system 16 when the user's vital signs are substantially unchanged. Access terminal 17 may then provide a second level of security by ensuring that the access signal is an authorized access signal for secure system 16 before granting access to secure system 16 for the authenticated user.

The disclosed techniques may protect against the scenario in which computing device 16 is lost or stolen, and an unauthorized user attempts to gain access to secure system 16 using computing device 12. In this scenario, computing device 12 may be unable to receive vital signs of the unauthorized user from wearable device 14, or computing device 12 may detect vital signs from the unauthorized user that are indicative of stress or nervousness or that do not match expected vital signs of the authorized user. In any of these cases, computing device 12 may not send the access signal to access terminal 17 for secure system 16, effectively denying access to secure system 16 for the unauthorized user. In other examples, wearable device 14 itself may operate as a secure access badge and communicate directly with access terminal 17 for secure system 16 via wireless signal 24 or network 10 (or another network not shown in FIG. 1) to gain access to secure system 16 for the user without need for computing device 12.

As a third example of the disclosed techniques, access terminal 17 for secure system 16 may receive an access signal from computing device 12 or wearable device 14 operating as a digital or virtual secure access badge for a user to gain access to secure system 16. In one example, access terminal 17 may be a physical security checkpoint and may receive communication, including the access signal, from computing device 12 via wireless signal 22 when within a certain distance or from wearable device 14 via wireless signal 24 when within a certain distance. In another example, access terminal 17 may be a virtual security checkpoint and may receive communication, including the access signal, from computing device 12 via network 10 based on a user input request or from wearable device 14 via network 10 (or another network not shown in FIG. 1) based on user input request. In some other examples, access terminal 17 may comprise a laser scanner configured to read the access signal when presented as a scannable image, e.g., a barcode or a QR code, on a display of computing device 12 or wearable device 14.

Access terminal 17 may authorize a user of computing device 12 or wearable device 14, and grant access to secure system 16 for the user based on the access signal matching one of a plurality of authorized access signals stored at access terminal 17. The techniques of this disclosure enable another factor to be included in the authentication of the user. According to the disclosed techniques, prior to granting access to secure system 16 for an authenticated user, access terminal 17 confirms that the user is not in distress when attempting to gain access to secure system 16 by monitoring the user's vital signs received from computing device 12 or directly from wearable device 14. For example, a spike in one of the user's vital signs, e.g., heart rate, may indicate that the user is nervous due to performing a nefarious action within secure system 16, or is being coerced or otherwise forced to gain access to secure system 16 by a bad actor. In this example, access terminal 17 denies access to secure system 16 for the authenticated user, and may alert a security officer or manager associated with secure system 16 of the failed access attempt. In other examples, access terminal 17 may further use the vital signs of the user received from computing device 12 or wearable device 14 to authenticate the identity of the user prior to granting access to secure system 16 for the user.

According to the disclosed techniques, access terminal 17 may provide a first level of security by ensuring that the received access signal is an authorized access signal for secure system 16. Access terminal 17 may then provide a second level of security by analyzing the user's vital signs to determine whether any spikes or sudden changes occur. Access terminal 17 may grant access to secure system 16 for the user when the user's vital signs are substantially unchanged.

The disclosed techniques may protect against the scenario in which computing device 12 or wearable device 14 operating as a secure access badge is lost or stolen, and an unauthorized user attempts to gain access to the secure system via access terminal 17 using computing device 12 or wearable device 14. In this scenario, access terminal 17 may be unable to receive vital signs of the unauthorized user, or access terminal 17 may detect vital signs from the unauthorized user that are indicative of stress or nervousness or that do not match expected vital signs of the authorized user. In any of these cases, access terminal 17 may deny access to secure system 16 for the unauthorized user.

As a fourth example of the disclosed techniques, computing device 12 and/or wearable device 14 may operate as a temporary credit or debit card having an additional level of security based on a user's vital signs to access the user's account at secure system 16 of a financial institution. As a fifth example of the disclosed techniques, computing device 12 and/or wearable device 14 may execute a virtual or digital wallet application that generates a unique signal based on a user's vital signs to authorize payment transactions at secure system 16 for a merchant or retailer. As a sixth example of the disclosed techniques, computing device 12 and/or wearable device 14 may execute a mobile banking application that authenticates a user based on the user's vital signs to access the user's account at secure system 16 of a financial institution. As a seventh example of the disclosed techniques, computing device 12 and/or wearable device 14 may execute a mobile banking application that triggers customer assistance for a user based on the user's vital signs while interacting with secure system 16 of a financial institution.

The architecture of network system 8 illustrated in FIG. 1 is shown for exemplary purposes only and network system 8 should not be limited to this architecture. Network system 8 illustrated in FIG. 1 shows a single wearable device 14 paired to a single computing device 12. In other examples, network system 8 may include multiple different wearable devices that may be "smart" or "dumb," and one or more of the different wearable devices may be paired to single computing device 12 or different computing devices. In other examples, network system 8 may include multiple secure systems 16 accessible by a user of single computing device 12 and/or single wearable device 14.

Figure 2:
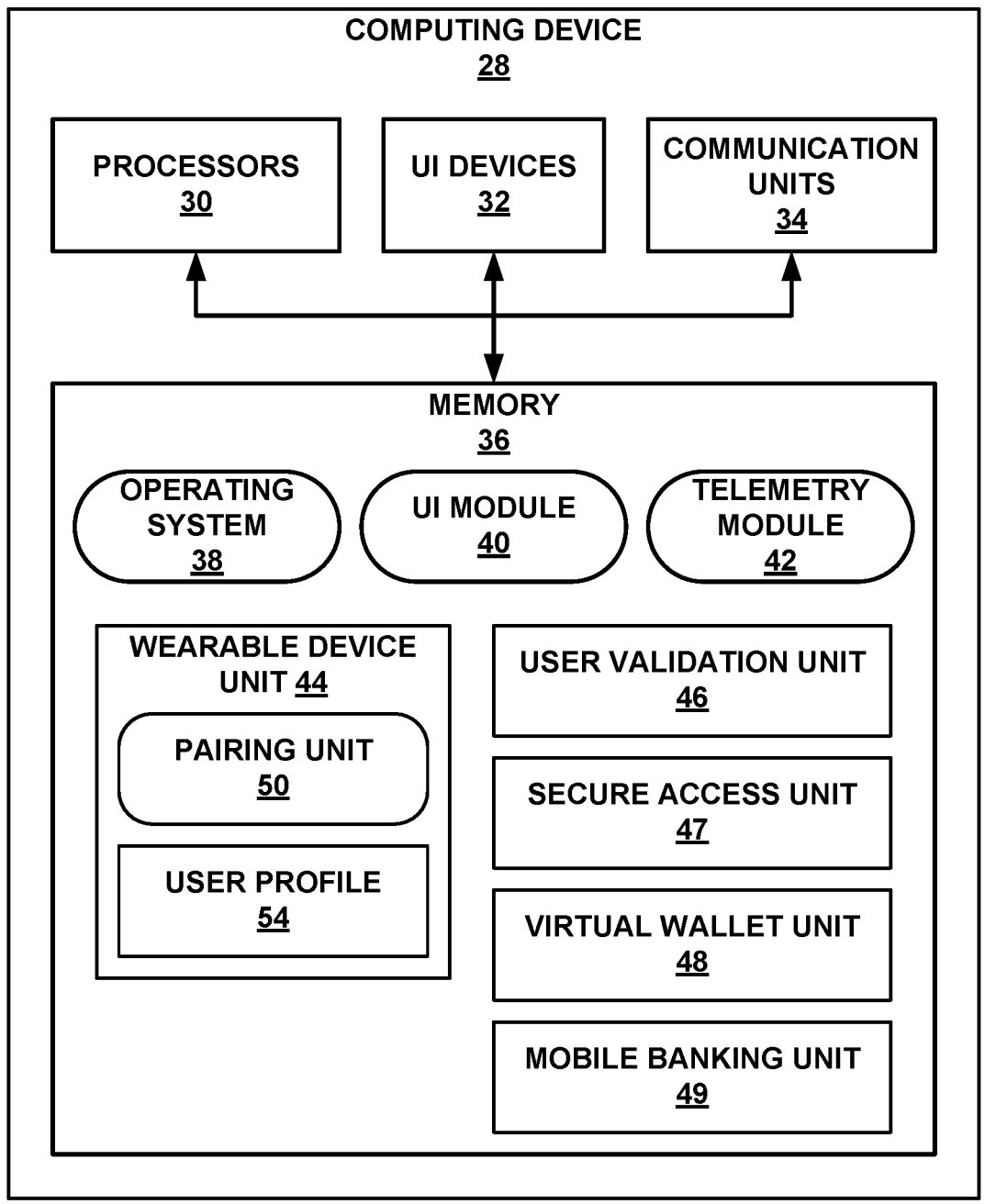
FIG. 2 is a block diagram illustrating an example computing device paired to a wearable device and configured to provide user access to a secure system, in accordance with the techniques of this disclosure.

FIG. 2 is a block diagram illustrating an example computing device 28 paired to a wearable device and configured to provide user access to a secure system, in accordance with the techniques of this disclosure. Computing device 28 may operate substantially similar to computing device 12 from FIG. 1. For example, computing device 28 may be paired to wearable device 14 from FIG. 1. In addition, computing device 28 may be in communication with secure system 16 from FIG. 1. The architecture of computing device 28 illustrated in FIG. 2 is shown for exemplary purposes only and computing device 28 should not be limited to this architecture. In other examples, computing device 28 may be configured in a variety of ways.

As shown in the example of FIG. 2, computing device 28 includes one or more processors 30, one or more user interface (UI) devices 32, one or more communication units 34, and one or more memory units 36. Memory 36 of computing device 28 includes operating system 38, UI module 40, telemetry module 42, wearable device unit 44, user validation unit 46, secure access unit 47, virtual wallet unit 48, and mobile banking unit 49, which are executable by processors 30. Each of the components, units or modules of computing device 28 are coupled (physically, communicatively, and/or operatively) using communication channels for inter-component communications. In some examples, the communication channels may include a system bus, a network connection, an inter-process communication data structure, or any other method for communicating data.

Processors 30, in one example, may comprise one or more processors that are configured to implement functionality and/or process instructions for execution within computing device 28. For example, processors 30 may be capable of processing instructions stored by memory 36. Processors 30 may include, for example, microprocessors, digital signal processors (DSPs), application specific integrated circuits (ASICs), field-programmable gate array (FPGAs), or equivalent discrete or integrated logic circuitry, or a combination of any of the foregoing devices or circuitry.

Memory 36 may be configured to store information within computing device 28 during operation. Memory 36 may include a computer-readable storage medium or computer-readable storage device. In some examples, memory 36 include one or more of a short-term memory or a long-term memory. Memory 36 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 36 is used to store program instructions for execution by processors 30. Memory 36 may be used by software or applications running on computing device 28 (e.g., wearable device unit 44, user validation unit 46, secure access unit 47, virtual wallet unit 48, or mobile banking unit 49) to temporarily store information during program execution.

Computing device 28 may utilize communication units 34 to communicate with external devices via one or more networks, e.g., network 10 from FIG. 1, or via wireless signals. Communication units 34 may be network interfaces, such as Ethernet interfaces, optical transceivers, radio frequency (RF) transceivers, or any other type of devices that can send and receive information. Other examples of interfaces may include Wi-Fi, NFC, or Bluetooth radios. In some examples, computing device 28 utilizes communication units 34 to wirelessly communicate with an external device, such as wearable device 14 or secure system 16 from FIG. 1.

UI devices 32 may be configured to operate as both input devices and output devices. For example, UI devices 32 may be configured to receive tactile, audio, or visual input from a user of computing device 28. In addition to receiving input from a user, UI devices 32 may be configured to provide output to a user using tactile, audio, or video stimuli. In one example, UI devices 32 may be configured to output content such as a GUI for display at a display device. UI devices 32 may include a presence-sensitive display that displays a GUI and receives input from a user using capacitive, inductive, and/or optical detection at or near the presence sensitive display.

Other examples of UI devices 32 include a mouse, a keyboard, a voice responsive system, video camera, microphone or any other type of device for detecting a command from a user, or a sound card, a video graphics adapter card, or any other type of device for converting a signal into an appropriate form understandable to humans or machines. Additional examples UI devices 32 include a speaker, a cathode ray tube (CRT) monitor, a liquid crystal display (LCD), organic light emitting diode (OLED), or any other type of device that can generate intelligible output to a user.

Operating system 38 controls the operation of components of computing device 28. For example, operating system 38, in one example, facilitates the communication of UI module 40, telemetry module 42, wearable device unit 44, user validation unit 46, secure access unit 47, virtual wallet unit 48, and mobile banking unit 49 with processors 30, UI devices 32, communication units 34, and memory 36. UI module 40, telemetry module 42, wearable device unit 44, user validation unit 46, secure access unit 47, virtual wallet unit 48, and mobile banking unit 49 may each include program instructions and/or data stored in memory 36 that are executable by processors 30. For example, user validation unit 46 and secure access unit 47 may each include instructions that cause computing device 28 to perform one or more of the techniques described in this disclosure.

Computing device 28 may include additional components that, for clarity, are not shown in FIG. 2. For example, computing device 28 may include a battery to provide power to the components of computing device 28. Similarly, the components of computing device 28 shown in FIG. 2 may not be necessary in every example of computing device 28.

In the example illustrated in FIG. 2, wearable device unit 44 includes a pairing unit 50 and at least one user profile 54. Wearable device unit 44 of computing device 28 is configured to manage pairings or links to one or more wearable devices, e.g., wearable device 14 from FIG. 1, that may operate as accessories of wearable device 28. Pairing unit 50 of wearable device unit 44 may be configured to establish a pairing between computing device 28 and a wearable device by initiating communication with the wearable device via communication units 34. For example, pairing unit 50 may communicate with the wearable device using a short-range wireless communication protocol when the wearable device is within a certain distance, e.g., less than 100 meters in the case of Bluetooth. In other examples, instead of using a short-range wireless communication protocol, pairing unit 50 may pair computing device 28 to the wearable device using an online dashboard or interface via a browser or other application executed by processors 30. Pairing unit 50 may exchange some information with the wearable device to establish the pairing, such as identification information and/or communication capabilities. In addition, pairing unit 50 may periodically send "keepalive" messages to the wearable device to maintain the pairing. Based on this pairing, computing device 28 recognizes and communicates with the wearable device whenever the wearable device is within range for the short-range wireless communication protocol.

Wearable device unit 44 may receive one or more vital signs of a user from the wearable device, and wearable device unit 44, or other applications executed by processors 30, may store, analyze, output, and communicate the received vital signs. In one example, computing device 28 may be a smart phone executing a health or fitness application and the wearable device may be in the form of an electronic bracelet or an electronic tattoo worn by a user to collect or monitor a user's vital signs for use by the health or fitness application on computing device 28. Wearable device unit 44 may receive the monitored vital signs from the wearable device, and store the monitored information of the user in user profile 54. In some examples, user profile 54 may comprise a historic profile that tracks the user's vital signs over time. In other examples, user profile 54 may comprise a real-time profile that stores a discrete set of the user's vital signs at a given point in time. Wearable device unit 44 may also perform some analysis based on the monitored vital signs, and output the results to the user via UI devices 32.

According to the techniques described in this disclosure, computing device 28 uses the one or more vital signs of a user received from a paired wearable device, e.g., wearable device 14 from FIG. 1, to request access to a secure system, e.g., secure system 16 from FIG. 1, for the user.

In accordance with one of the disclosed techniques, user validation unit 46 of computing device 28 is configured to automatically validate a user of computing device 28 as a person and not a robot to a secure system based on receipt of the user's vital signs from a paired wearable device. User validation unit 46 may provide the validation in response to a validation request received from a secure system, e.g., a CAPTCHA request prompt at a secure payment portal of an online retailer's website. In this way, instead of a user having to manually type displayed letters, numbers, or characters, or manually select an image, in response to the CAPTCHA request, user validation unit 46 detects one or more vital signs of the user from the paired wearable device to automatically validate that the user is a person.

For example, when the user logs into the online retailer's website via a browser or other application executed by processors 30 on computing device 28, computing device 28 may receive the CAPTCHA request prompt prior to accessing the secure payment portal of the website. In response to the CAPTCHA request prompt, user validation unit 46 listens for the one or more vital signs from the wearable device. In some examples, in response to the CAPTCHA request prompt, a user of computing device 28 may select an automatic validation option, e.g., an "eCAPTCHA" option, to activate user validation unit 46 to perform the automatic user validation.

To validate the user as a person, user validation unit 46 may first confirm that the wearable device is paired to computing device 28. For example, user validation unit 46 may communicate with wearable device unit 44 to determine whether the wearable device in communication with computing device 28 is one of the wearable devices that are paired or linked to computing device 28. In other words, user validation unit 46 confirms that the wearable device in communication with computing device 28 is the "correct" wearable device that is associated with the user of computing device 28.

Second, user validation unit 46 may confirm that the one or more vital signs are being actively received from the paired wearable device. In some examples, user validation unit 46 may retrieve the one or more vital signs from another application executed on computing device 28 that is already receiving the vital signs for another purpose, e.g., health or fitness tracking. In other examples, user validation unit 46 may activate an interface included in communication units 34 to communicate with the paired wearable device, and request the one or more vital signs from the paired wearable device exclusively for user validation.

User validation unit 46 may listen to a relatively short snippet of the received vital signs, e.g., 1, 5, or 10 seconds, to validate the user as a person and not a robot. In some examples, after the initial user validation, user validation unit 46 may continuously monitor the user's vital signs during a session with the secure system, e.g., during a payment transaction with the online merchant's secure payment portal, to ensure that a person, or in some cases the same person, is accessing the secure system over the entire session. This continuous monitoring during the secure session enables user validation unit 46 to avoid the need to re-validate or re-authenticate the user in the case of multiple secure transactions being performed during the same session.

In some cases, user validation unit 46 may detect a sudden disappearance or disruption in the user's vital signs during the session, which may indicate that the paired wearable device was detached from the user. In this case, the session with the secure system ends. In other cases, user validation unit 46 may detect the disruption in the user's vital signs followed by a reappearance of a different set of vital signs during the session, which may indicate that the paired wearable device was detached from the user and then attached to an unauthorized user. In this case, the session with the secure system also ends, and the user will need to re-validate or re-authenticate.

According to the disclosed techniques, the active receipt of any vital signs from the paired wearable device may be enough to validate the user as a person and not a robot. In other words, the received vital signs may not necessarily be used to authenticate an identity of the user as a specific person, but instead are used to determine that the current user of computing device 28 is a living person. In other examples, user validation unit 46 may compare the received vital signs against user profile 54 to first authenticate the identity of the specific user, and then validate that the specific user is a person. User validation unit 46 may In the case where computing device 28 cannot connect to the wearable device, user validation unit 46 may send a notification to the user of computing device 28 via UI devices 32, e.g., as an email, a text message, or a push notification, to re-pair the wearable device to computing device 28. In addition, user validation unit 46 may send a notification to the user of computing device 28 indicating that the user cannot be automatically validated as a person to the secure system. The notification may indicate additional steps to be performed for user validation, including manual CAPTCHA. For example, user validation unit 46 may send a request to the user via UI devices 32 for user input, e.g., manually typed characters or a manually selected image, to manually validate the user as a person to the secure system.

In accordance with another one of the disclosed techniques, secure access unit 47 of computing device 28 is configured to operate as a secure access badge to request access to a secure system for a user based on one or more vital signs of the user received from a paired wearable device. Secure access unit 47 may use the received vital signs from the paired wearable device to provide an extra level of security prior to emitting an access signal requesting access to the secure system for the user. For example, secure access unit 47 may act as a first level of security by analyzing the received vital signs of received vital signs to confirm that the user is not in distress when attempting to gain access to the secure system. In the case where the user's vital signs are substantially unchanged, e.g., no spikes or sudden changes in the vital signs, secure access unit 47 sends the access signal to an access terminal for the secure system.

In other examples, described in more detail below with respect to access terminal 80 from FIG. 4, secure access unit 47 of computing device 28 may pass the one or more vital signs received from the paired wearable device to a secure system along with the access signal. An access terminal, e.g., access terminal 80, of the secure system may then determine whether to grant access to the user based on both the user's vital signs and the access signal.

In some examples, secure access unit 47 may be configured to detect a geolocation of computing device 28 and initiate communication with a physical access terminal of a secure location or at a computer terminal used to access a secure computing system when computing device 28 is within a certain distance of the physical access terminal. In other examples, secure access unit 47 may receive a user input request from the user of computing device 28 via UI devices 32 and, in response, initiate communication with a virtual access terminal at a login to a secure computing system or a secure database. In either of these examples, secure access unit 47 also receives one or more vital signs of the user from the paired wearable device. Secure access unit 47 may retrieve the one or more vital signs from another application executed on computing device 28 that is already receiving the vital signs for another purpose, or may request the one or more vital signs from the paired wearable device exclusively for secure access.

In one scenario, computing device 28 may be a smart phone of an employee who works in a high-security or high-risk area. Pairing unit 50 of computing device 28 may establish a pairing with a wearable device worn by the employee. When the employee is nearing a physical access terminal at an entrance to the high-security area in which the employee works, secure access unit 47 receives one or more vital signs of the user from the paired wearable device, and determines whether to emit an access signal to the access terminal based on the received vital signs. For example, secure access unit 47 compares the received vital signs of the employee against user profile 54 for the employee and, based on the vital signs substantially matching user profile 54, sends the access signal to the access terminal requesting access to the high-security area for the employee.

In the example where user profile 54 stores a real-time profile for the employee, secure access unit 47 may compare a current set of vital signs received from the paired wearable device against a previous, discrete set of vital signs included in user profile 54. In this example, secure access unit 47 may use a snapshot or a relatively short snippet of the currently received vital signs for comparison against the previous snapshot of the vital signs. In some cases, secure access unit 47 may determine whether an amount of change between the current set of vital signs and the previous set of vital signs is greater than or equal to a threshold amount. If the vital signs have not changed by at least the threshold amount, the vital signs are considered to substantially match user profile 54.

In the example where user profile 54 stores a historic profile that tracks the employee's vital signs over time, secure access unit 47 may compare the current set of vital signs received from the paired wearable device against the historic profile of vital signs included in user profile 54. In this example, secure access unit 47 may monitor the employee's vital signs over a longer period of time, e.g., 30 seconds to 1 minute or more, to determine whether the currently received vital signs match a pattern of the employee's historic profile. By comparing the currently received vital signs against the historic profile, secure access unit 47 may determine whether the current vital signs indicate that the employee is in duress and, further, may authenticate the identity of the employee based on the historic profile of the employee included in user profile 54.

In the case where the vital signs do not match user profile 54, secure access unit 47 does not send the access signal to the access terminal for the high-security area, effectively denying the employee access to the high-security area unless another step is taken, e.g., a visual check of the employee by a security officer or manager associated with the high-security area. In some examples, secure access unit 47 may send a signal to the access terminal requesting a visual check of the employee. The visual check may be performed in person or via a video conference or video chat application executed by processors 30 on computing device 28. In some examples, to assist the security officer or manager, secure access unit 47 may include an indication of the employee's geolocation and/or an indication of a computer system last accessed by the employee with the signal requesting the visual check.

In some examples, once the employee is granted access to the high-security area, secure access unit 47 may continuously monitor the employee's vital signs during a session within the high-security area to ensure that the same authenticated employee is accessing the high-security area over the entire session, and/or to ensure that the authenticated employee is not performing any nefarious action when within the high-security area. If a spike or sudden change is detected in the employee's vital signs, secure access unit 47 may send a denial of access signal to the access terminal requesting that access to the high-security area be denied or revoked for the employee and that any secure computing system being accessed by the employee are locked down. In some cases, secure access unit 47 may also send the signal to the access terminal requesting a visual check of the employee. Secure access unit 47 may send similar signals to the access terminal upon detection of a sudden disappearance or disruption in the user's vital signs and/or a reappearance of a different set of vital signs during the session within the high-security area.

In accordance with an additional one of the disclosed techniques, virtual wallet unit 48 of computing device 28 is configured to perform payment transactions for a user based on one or more vital signs of the user received from a paired wearable device. Virtual wallet unit 48 may store one or more user selectable virtual assets for the performance of online transactions via a website, a point of sale (POS) device, or another external device. Virtual wallet unit 48 may include a plurality of virtual financial assets having individual assigned values and/or a plurality of virtual non-financial assets used to perform the online transactions. Each of the virtual financial assets included in virtual wallet unit 48 may correspond to a financial asset held by a financial institution, and each of the virtual non-financial assets included in virtual wallet unit 48 may correspond to a document, e.g., an identification card, held by the user.

In one example, virtual wallet unit 48 may include a temporary card as a replacement for a lost or stolen credit or debit card of the user. Instead of waiting several days to receive a new debit or credit cards, the disclosed techniques may immediately provide the user with a virtual replacement card having an extra level of security based on the user's vital signs received from a paired wearable device. In some cases, the user's financial institution may provide the user with the wearable device, e.g., an electronic sticker or tattoo, to be paired with computing device 28 for the exclusive purpose of authenticating transactions made by virtual wallet unit 48 using the temporary card. In other cases, the user may allow virtual wallet unit 48 access to the user's existing wearable device to authenticate transactions made the temporary card.

The user may use the temporary card to perform transactions online, via a mobile device, at an automatic teller machine (ATM), or through digital pay as long as the wearable device is attached and monitoring vital signs of the user. If the wearable device stops monitoring vital signs for a certain length of time or if there is an interruption followed by receipt of vital signs that are substantially different than pre-interruption readings, virtual wallet unit 48 may automatically shut down the temporary card. In addition, if an unauthorized user attempts to use the temporary card without the paired wearable device, virtual wallet unit 48 may automatically shut down the temporary card. Virtual wallet unit 48 may also send a notification to the user of computing device 28 via UI devices 32 informing the user of the termination. This concept of a temporary card tied to a wearable device may also be useful in a corporate setting in which employees make daily transactions with large sums of money or high-risk data. This concept may also be useful at resorts or theme parks in which temporary accounts may be set up to track customers' purchases and access to rooms, attractions, or other areas. Additionally, this concept may be useful for parents to give their children temporary access to money for field trips and other events.

In another example, virtual wallet unit 48 may be configured as a digital pay application executed by processors 30 on computing device 28 having an extra level of security. A user of computing device 28 may opt in with the user's financial institution to have multifactor authentication for digital transactions performed with virtual wallet unit 48 based on one or more vital signs being received from the paired wearable device.

At set-up, the user may register computing device 28 and/or virtual wallet unit 48 with the financial institution for digital payments. In some cases, the financial institution may provide the user with the wearable device to be paired with computing device 28 for the exclusive purpose of digital pay. In other cases, the user may allow virtual wallet unit 48 access to the user's existing wearable device for digital pay. In some examples, one of the user's vital signs, e.g., a heartbeat, may be turned into a unique signal for the user. When the user is logged in, virtual wallet unit 48 may listen for the unique signal being emitted by the wearable device. If the user's unique signal is not present or if another signal is present, virtual wallet unit 48 may not allow a payment transaction to occur without additional steps to authenticate the transaction.

In accordance with another one of the disclosed techniques, mobile banking unit 49 of computing device 28 is configured to perform behavioral authentication and/or trigger behavioral assistance for a user based on one or more vital signs of the user received from a paired wearable device. In one example, mobile banking unit 49 may tie a user's vital signs to the user's financial behavior profile for authentication purposes. In this example, the user's financial institution may create a profile of transactional behavior for the user based on existing financial data. Additionally, the financial institution may take a baseline of the user's vital signs for different transactions during setup with the paired wearable device.

When the user takes out a larger amount of money than normal at an ATM, or performs some other transaction that is different than the user's typical financial behavior, and the user's vital signs are substantially different than the baseline vital signs for the transaction, mobile banking unit 49 may not authenticate the user with the financial institution to perform the transaction. In some examples, the attempted transaction may be delayed and the user may need to take additional steps, e.g., answer a security question on a second registered device, to be authenticated to perform the transaction. The user may also receive a call or notification on computing device 28 or another registered device from a security/fraud department associated with the financial institution.

In another example, mobile banking unit 49 may trigger a request for assistance from a customer service representative at a user's financial institution based on a substantial change in the user's vital signs. For example, mobile banking unit 49 may monitor one or more vital signs of the user received from the paired wearable device while the user is interacting with applications, systems, and/or stores associated with the user's financial institution. If the user is logged into mobile banking unit 49 executed by processors 30 on computing device 28 and the wearable device is paired to computing device 28, mobile banking unit 49 may monitor the user's vital signs.

During the user's engagement with the mobile banking application, if mobile banking unit 49 detects a spike or sudden change in the user's vital signs, which may indicate frustration or anger, mobile banking unit 49 may send a request for a customer service representative at the financial institution to check on the user. For example, mobile banking unit 49 may send an alert to the customer representative to perform the customer check including a notice of the vital sign spike and an indication of what the customer was logged into (e.g., bill pay, transfers, etc.) at the time of the vital sign spike. The customer representative may perform the customer check via a live chat or a video chat via computing device 28.

In some examples, a similar process of triggering a customer service check may be performed at an ATM or even on a customer service line after authentication. In stores, an alert may result in a teller or manager assisting a customer sooner, or it may change how the teller or manager interacts with the customer. For example, a loan consultant may give more time and attention to an applicant with a vital sign spike alert. As another example, a manager may ask additional questions when closing an account to make sure the customer is not doing so under duress based on the user's vital signs. Alternatively, as described above, the user may already have a real-time ongoing financial behavior profile with the financial institution. In this case, a customer service representative or an employee may take certain actions to authenticate and assist the user based on the user's vital signs and behavior (both financial and personal) being substantially different than the user's profiles. After an initial interaction with the user, the customer service representative may also reply to the original customer check alert with a word, such as nervous or frustrated, to get more guidance on how to assist the user.

For any of the above described examples of the techniques of this disclosure, in the case where computing device 28 is communicating with an unpaired or "wrong" wearable device or cannot receive the one or more vital signs from the wearable device after a preset number of tries, wearable device unit 44 may lock down one or more of user verification unit 46, secure access unit 47, virtual wallet unit 48, and mobile banking unit 49 until the user performs additional steps, e.g., answering a security question or inputting a code, and/or re-pairs the wearable device to computing device 28. In addition, wearable device unit 44 may send a notification to the user of computing device 28 via UI devices 32 indicating that an unauthenticated transaction was attempted and/or the wearable device did not match one of the paired wearable devices for computing device 28.

Figure 3:
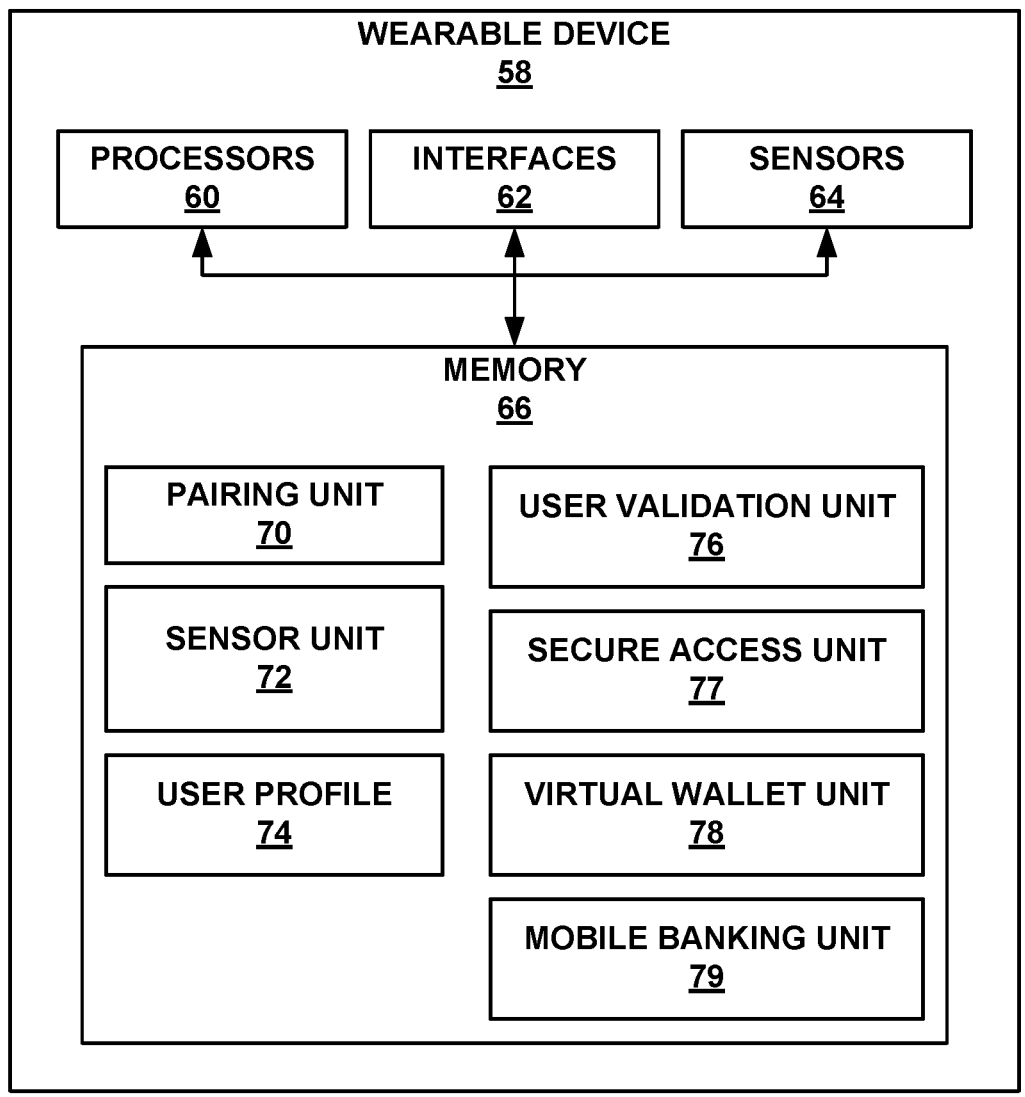
FIG. 3 is a block diagram illustrating an example wearable device configured to provide user access to a secure system, in accordance with the techniques of this disclosure.

FIG. 3 is a block diagram illustrating an example wearable device 58 configured to provide user access to a secure system, in accordance with the techniques of this disclosure. Wearable device 58 may operate substantially similar to wearable device 14 from FIG. 1. Wearable device 58 may be paired to computing device 12 from FIG. 1 or computing device 28 from FIG. 2. In addition, wearable device 58 may be in communication with secure system 16 from FIG. 1. The architecture of wearable device 58 illustrated in FIG. 3 is shown for exemplary purposes only and wearable device 58 should not be limited to this architecture. In other examples, wearable device 58 may be configured in a variety of ways.

As shown in the example of FIG. 3, wearable device 58 includes one or more processors 60, one or more interfaces 62, one or more sensors 64, and one or more memory units 66. Wearable device 58 also includes pairing unit 70, sensor unit 72, user profile 74, user validation unit 76, secure access unit 77, virtual wallet unit 78, and mobile banking unit 79, each of which may be implemented as program instructions and/or data stored in memory 66 and executable by processors 60 or implemented as one or more hardware units or devices of wearable device 58. In some examples, memory 66 of wearable device 58 may also store an operating system executable by processors 60. The operating system stored in memory 66 may control the operation of components of wearable device 58. The components, units or modules of wearable device 60 are coupled (physically, communicatively, and/or operatively) using communication channels for inter-component communications. In some examples, the communication channels may include a system bus, an inter-process communication data structure, or any other method for communicating data.

Processors 60, in one example, may comprise one or more processors that are configured to implement functionality and/or process instructions for execution within wearable device 58. For example, processors 60 may be capable of processing instructions stored by memory 66. Processors 60 may include, for example, microprocessors, DSPs, ASICs, FPGAs, or equivalent discrete or integrated logic circuitry, or a combination of any of the foregoing devices or circuitry.

Memory 66 may be configured to store information within wearable device 58 during operation. Memory 66 may include a computer-readable storage medium. In some examples, memory 66 includes one or more of a short-term memory or a long-term memory. Memory 66 may include, for example, RAM, DRAM, SRAM, flash memories, or forms of EPROM or EEPROM. In some examples, memory 66 is used to store program instructions for execution by processors 60. Memory 66 may be used by software running on wearable device 58 (e.g., pairing unit 70, sensor unit 72, user validation unit 76, secure access unit 77, virtual wallet unit 78, and mobile banking unit 79) to temporarily store information during program execution.

Wearable device 58 may utilize interfaces 62 to communicate with external devices via one or more networks, e.g., network 10 from FIG. 1, or via wireless signals. Interfaces 66 may be network interfaces, such as Ethernet interfaces, optical transceivers, RF transceivers, or any other type of devices that can send and receive information. Other examples of interfaces may include Wi-Fi, NFC, or Bluetooth radios. In some examples, wearable device 58 utilizes interfaces 62 to wirelessly communicate with an external device such computing device 12 or secure system 16 from FIG. 1.

Wearable device 58 may also utilize interfaces 62 to communicate with users of wearable device 58. Interfaces 62 may be UI devices configured to operate as both input devices and output devices. For example, the UI devices may be configured to receive tactile, audio, or visual input from a user of wearable device 58. In addition to receiving input from a user, the UI devices may be configured to provide output to a user using tactile, audio, or video stimuli. In one example, the UI devices may be configured to output content for display, e.g., a GUI, in accordance with a user interface unit stored in memory 66. In this example, the UI devices may include a presence-sensitive display that displays a GUI and receives input from a user using capacitive, inductive, and/or optical detection at or near the presence sensitive display. Other examples of the UI devices include a mouse, a keyboard, a voice responsive system, video camera, microphone or any other type of device for detecting a command from a user, or a sound card, a video graphics adapter card, or any other type of device for converting a signal into an appropriate form understandable to humans or machines. Additional examples of the UI devices include a speaker, a CRT monitor, a LCD, OLED, or any other type of device that can generate intelligible output to a user.

Sensors 64 may be used to monitor vital signs and/or behavior biometrics of a user while wearing wearable device 58. In some examples, sensors 64 may comprise conducting elements that are in contact with a portion of the user's body to collect the user's vital signs, such as heart rate, breathing rate, blood pressure, or body temperature. In other examples, sensors 64 may comprise pedometers, accelerometers, microphones, cameras, or the like, to collect the user's behavior biometrics, e.g., gait, voice, or speed of typing, talking or texting.

Wearable device 58 may include additional components that, for clarity, are not shown in FIG. 3. For example, wearable device 58 may include a battery to provide power to the components of wearable device 58. Similarly, the components of wearable device 58 shown in FIG. 3 may not be necessary in every example of wearable device 58.

In the example illustrated in FIG. 3, wearable device 58 includes a pairing unit 70, a sensor unit 72, and a user profile 74. Pairing unit 70 of wearable device 58 may establish a pairing between wearable device 58 and a computing device, e.g., computing device 12 from FIG. 1. For example, pairing unit 70 may initiate communication with the computing device using a short-range wireless communication protocol when the computing device is within a certain distance, e.g., less than 100 m in the case of Bluetooth. In other examples, instead of using a short-range wireless communication protocol, pairing unit 70 may pair wearable device 58 to the computing device using an online dashboard or interface via a browser or other application executed by processors 60. In addition, in some examples, pairing unit 70 may also be configured to establish a pairing between wearable device 58 and a secure system, e.g., secure system 16 from FIG. 1. In general, pairing unit 70 of wearable device 58 may operate substantially similar to pairing unit 50 of computing device 28 from FIG. 2.

Sensor unit 72 may monitor one or more vital signs of the user received from sensors 64, and store the monitored vital signs of the user in at least one user profile 74. User profile 74 may track at least one vital sign of the user of wearable device 14. In some examples, user profile 74 may comprise a historic profile that tracks the user's vital signs over time. In other examples, user profile 74 may comprise a real-time profile that stores a discrete set of the user's vital signs at a given point in time. In one scenario, sensor unit 72 may output the monitored vital signs to a paired external device, e.g., computing device 12 or secure system 16 from FIG. 1, via interfaces 62 for analysis of the monitored vital signs. In another scenario, sensor unit 72, or other applications executed by processors 60, may analyze, output, and communicate the monitored vital signs. For example, wearable device 58 may be a smart watch executing a health or fitness application, and collecting or monitoring a user's vital signs for use by the health or fitness application.

According to the techniques described in this disclosure, wearable device 58 uses the one or more vital signs of a user received from sensors 64 to request access to a secure system, e.g., secure system 16 from FIG. 1, for the user.

In accordance with one of the disclosed techniques, user validation unit 76 of wearable device 58 is configured to automatically validate a user of wearable device 58 as a person and not a robot to a secure system based on receipt of the user's vital signs from sensors 64. User validation unit 76 may provide the validation in response to a validation request received from a secure system, e.g., a CAPTCHA request prompt at a secure payment portal of an online retailer's website. To validate the user as a person to the secure system, user validation unit 76 may confirm that the one or more vital signs of the user are being received from sensors 64. For example, user validation unit 76 may retrieve the one or more vital signs from sensor unit 72 and/or from sensors 64.

In the case where user validation unit 76 cannot receive the one or more vital signs from sensors 64, user validation unit 76 may send a notification to the user of wearable device 58 via interfaces 62, e.g., as an email, a text message, or a push notification, indicating that the user cannot be automatically validated as a person to the secure system. The notification may indicate additional steps to be performed for user validation, including manual CAPTCHA. In general, user validation unit 76 of wearable device 58 operates substantially similar to user validation unit 46 of computing device 28 described above with respect to FIG. 2, with the exception that user validation unit 76 receives the user's vital signs directly from sensors 64 included on wearable device 58 instead of from a paired external device.

In accordance with another one of the disclosed techniques, secure access unit 77 of wearable device 58 is configured to operate as a secure access badge to request access to a secure system for a user based on one or more vital signs of the user received from sensors 64. Secure access unit 77 may use the received vital signs from sensors 64 to provide an extra level of security prior to emitting an access signal requesting access to the secure system for the user. For example, secure access unit 77 may act as a first level of security by analyzing the received vital signs to confirm that the user is not in distress when attempting to gain access to the secure system. In the case where the user's vital signs substantially match those stored in user profile 74 for the user, e.g., no spikes or sudden changes in the vital signs, secure access unit 77 sends the access signal to an access terminal for the secure system.

In the case where the vital signs do not match user profile 74, secure access unit 77 does not send the access signal to the access terminal for the secure system, effectively denying the user access to the secure system unless another step is taken, e.g., a visual check of the user by a security officer or manager associated with the high-security area. In some examples, secure access unit 77 may send a signal to the access terminal requesting a visual check of the employee. In general, secure access unit 77 of wearable device 58 operates substantially similar to secure access unit 47 of computing device 28 described above with respect to FIG.

2, with the exception that secure access unit 77 receives the user's vital signs directly from sensors 64 included on wearable device 58 instead of from a paired external device.

In accordance with an additional one of the disclosed techniques, virtual wallet unit 78 of wearable device 58 is configured to perform payment transactions for a user based on one or more vital signs of the user received from sensors 64. In one example, virtual wallet unit 78 may include a temporary card as a replacement for a lost or stolen credit or debit card of the user. In this example, wearable device 58 may itself be the replacement card having an extra level of security based on the user's vital signs received from sensors 64. In some cases, virtual wallet unit 78 may output a scannable unique code or emit a signal that can be read by a POS device, an ATM, or another external device. If wearable device 58 becomes detached from the user such that virtual wallet unit 78 is no longer receiving vital signs from sensors 64, virtual wallet unit 78 may deactivate the temporary account and notify the user of the termination via interfaces 62.

In another example, virtual wallet unit 78 may be configured as a digital pay application executed by processors 60 on wearable device 58. The user of wearable device 58 may opt in with the user's financial institution to have multifactor authentication for digital transactions performed with virtual wallet unit 78 based on one or more vital signs being received from sensors 64. In general, virtual wallet unit 78 of wearable device 58 operates substantially similar to virtual wallet unit 48 of computing device 28 described above with respect to FIG. 2, with the exception that virtual wallet unit 78 receives the user's vital signs directly from sensors 64 included on wearable device 58 instead of from a paired external device.

In accordance with another one of the disclosed techniques, mobile banking unit 79 of wearable device 58 is configured to perform behavioral authentication and/or trigger behavioral assistance for a user based on one or more vital signs of the user received from sensors 64. In one example, mobile banking unit 79 may tie a user's vital signs to the user's financial behavior profile for authentication purposes. In another example, mobile banking unit 79 may trigger a request for assistance from a customer service representative at a user's financial institution based on a substantial change in the user's vital signs. In general, mobile banking unit 79 of wearable device 58 operates substantially similar to mobile banking 49 of computing device 28 described above with respect to FIG. 2, with the exception that mobile banking unit 79 receives the user's vital signs directly from sensors 64 included on wearable device 58 instead of from a paired external device.

Figure 4:
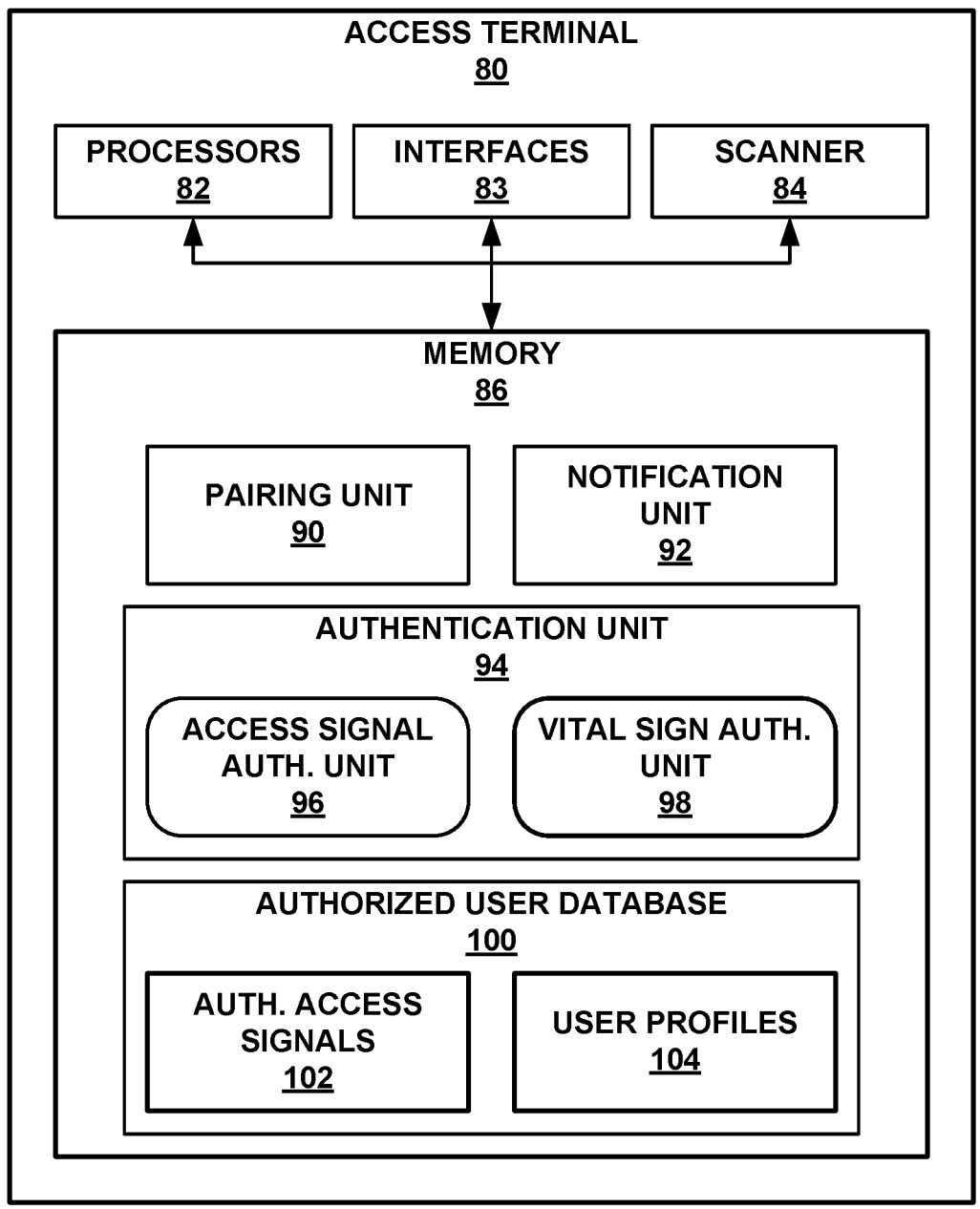
FIG. 4 is a block diagram illustrating an example access terminal for a secure system configured to authenticate a user for access to the secure system, in accordance with the techniques of this disclosure.

FIG. 4 is a block diagram illustrating an example access terminal 80 for a secure system configured to authenticate a user for access to the secure system, in accordance with the techniques of this disclosure. Access terminal 80 may operate substantially similar to access terminal 17 for secure system 16 from FIG. 1. Access terminal 80 may be in communication with computing device 12 from FIG. 1 or computing device 28 from FIG. 2. In addition, access terminal 80 may also be in communication with wearable device 14 from FIG. 1 or wearable device 58 from FIG. 3. The architecture of access terminal 80 illustrated in FIG. 4 is shown for exemplary purposes only and access terminal 80 should not be limited to this architecture. In some examples, access terminal 80 may include additional components that, for clarity, are not shown in FIG. 4. In other examples, access terminal 80 may be configured in a variety of ways.

As shown in the example of FIG. 4, access terminal 80 may include one or more processors 82, one or more interfaces 83, at least one scanner 84, and one or more memory units 86. Access terminal 80 also includes pairing unit 90, notification unit 92, authentication unit 94, and authorized user database 100, each of which may be implemented as program instructions and/or data stored in memory 86 and executable by processors 82 or implemented as one or more hardware units or devices of access terminal 80. In some examples, memory 86 of access terminal 80 may also store an operating system executable by processors 82. The operating system stored in memory 86 may control the operation of components of access terminal 80. The components, units or modules of access terminal 80 are coupled (physically, communicatively, and/or operatively) using communication channels for inter-component communications. In some examples, the communication channels may include a system bus, an inter-process communication data structure, or any other method for communicating data.

Processors 82, in one example, may comprise one or more processors that are configured to implement functionality and/or process instructions for execution within access terminal 80. For example, processors 82 may be capable of processing instructions stored by memory 86. Processors 82 may include, for example, microprocessors, DSPs, ASICs, FPGAs, or equivalent discrete or integrated logic circuitry, or a combination of any of the foregoing devices or circuitry.

Memory 86 may be configured to store information within access terminal 80 during operation. Memory 86 may include a computer-readable storage medium. In some examples, memory 86 includes one or more of a short-term memory or a long-term memory. Memory 86 may include, for example, RAM, DRAM, SRAM, flash memories, or forms of EPROM or EEPROM. In some examples, memory 86 is used to store program instructions for execution by processors 82. Memory 86 may be used by software running on access terminal 80 (e.g., pairing unit 90, notification unit 92, or authentication unit 94) to temporarily store information during program execution.

Access terminal 80 may utilize interfaces 83 to communicate with external devices via one or more networks, e.g., network 10 from FIG. 1, or via wireless signals. Interfaces 83 may be network interfaces, such as Ethernet interfaces, optical transceivers, RF transceivers, or any other type of devices that can send and receive information. Other examples of interfaces may include Wi-Fi, NFC, or Bluetooth radios. In some examples, access terminal 80 utilizes interfaces 83 to wirelessly communicate with an external device such computing device 12 or wearable device 14 from FIG. 1.

Scanner 84 may be used to scan or otherwise read an access signal from an external device such computing device 12 or wearable device 14 from FIG. 1. In some examples, scanner 84 may comprise a laser scanner that is capable of reading a scannable image, e.g., a barcode or a QR code, presented on a display of a computing device or a wearable device.

Access terminal 80 may include additional components that, for clarity, are not shown in FIG. 4. For example, access terminal 80 may include a battery to provide power to the components of access terminal 80. Similarly, the components of access terminal 80 shown in FIG. 4 may not be necessary in every example of access terminal 80. In some examples, access terminal 80 may be a physical security checkpoint at the entrance of a secure building or a secure area within a building, or at a computer terminal used to access a secure computing system. In other examples, access terminal 80 may be a virtual security checkpoint at a login to a secure computing system.

Pairing unit 90 of access terminal 80 may establish a pairing between access terminal 80 and a computing device or a wearable device. For example, pairing unit 90 may initiate communicate with a wearable device using a short-range wireless communication protocol when the wearable device is within a certain distance, e.g., less than 20 cm in the case of NFC. In other examples, instead of using a short-range wireless communication protocol, pairing unit 90 may pair access terminal 80 to the wearable device using an online dashboard or interface via a browser or other application executed by processors 82. In addition, in some examples, pairing unit 90 may also be configured to establish a pairing between access terminal 80 and a computing system that is in turn paired to the wearable device.

In the example illustrated in FIG. 4, authentication unit 94 of access terminal 80 includes an access signal authentication unit 96 and a vital sign authentication unit 98. Authentication unit 94 may receive an access signal requesting access to a secure system from a computing device operating as a digital or virtual secure access badge for a user of the computing device, and may also receive one or more vital signs of the user from the computing device. According to the disclosed techniques, authentication unit 94 may authenticate the user of the computing device and grant access to a secure system for a user based on both the access signal and the one or more vital signs of the user. In this example, the computing device may be either a computing device that is paired to a wearable device from which it receives the user's vital signs, or the wearable device itself.

Authentication unit 94 may use the received vital signs from the computing device to provide an extra level of security when granting access to the secure system. Access signal authentication unit 96 may act as a first level of security by ensuring that the received access signal is an authorized access signal for the secure system. For example, access signal authentication unit 96 may compare the received access signal against a plurality of authorized access signals 102 stored in authorized user database 100 at access terminal 80. Access signal authentication unit 96 may then authenticate the user of the computing device based on the received access signal matching one of authorized access signals 102. In the case where the user cannot be authenticated based on the access signal, access terminal 80 may immediately deny access to the secure system for the user without analyzing the received vital signs of the user.

Vital sign authentication unit 98 of access terminal 80 may act as a second level of security by analyzing the user's vital signs to determine whether any spikes or sudden changes occur. Access terminal 80 may grant access to the secure system for the user when the user's vital signs are substantially unchanged. For example, vital sign authentication unit 98 may compare the one or more vital signs of the user against one of user profiles 104 for the authenticated user stored in authorized user database 100. In the case where user profiles 104 comprise real-time profiles for different users, vital sign authentication unit 98 may compare a current set of vital signs of the user against a previous set of vital signs included in the one of user profiles 104 for the authenticated user. In the case where user profiles 104 comprise historic profiles for different users, vital sign authentication unit 98 may compare the current set of vital signs of the user against the historic profile of vital signs included in the one of user profiles 104 for the authenticated user. In either of the above examples, vital sign authentication unit 98 may operate substantially similar to secure access unit 47 in computing device 28 from FIG. 2 to determine whether to grant access to the secure system for the user.

If the vital signs of the user are not substantially changed over those included in the one of user profiles 104 for the user, the vital signs are considered to substantially match the one of user profiles 104. In this scenario, authentication unit 94 of access terminal 80 grants access to the secure system for the authenticated user. In the scenario where the vital signs of the user do not match the one of user profiles 104, authentication unit 94 denies access to the secure system for the authenticated user unless additional steps are taken, e.g., a visual check of the user by a security officer or manager associated with the secure system. For example, notification unit 92 of access terminal 80 may send a prompt to the security officer or the manager requesting a visual check to verify the identity of the denied user. In some examples, to assist the security officer or manager, notification unit 92 may include the denied user's geolocation and/or a computer system last accessed by the denied user with the prompt requesting the visual check. In cases where the user's identity is verified by the visual check, the security officer or manager may override authentication unit 94 of access terminal 80 and manually grant access to the secure system for the authenticated user.

In some examples, upon granting access to the secure system for a session, vital sign authentication unit 98 may continuously monitor received vital signs during the session to ensure that the same authenticated user is accessing the secure system over the entire session and/or to ensure that the authenticated user is not performing any nefarious action when within the secure system. If a spike or sudden change is detected in the user's vital signs, authentication unit 94 may deny or revoke access to the secure system for the authenticated user. In addition, authentication unit 94 may lock down any secure computing system being accessed by the denied user. In some cases, notification unit 92 may also send the prompt requesting a visual check of the user.

Figure 5:
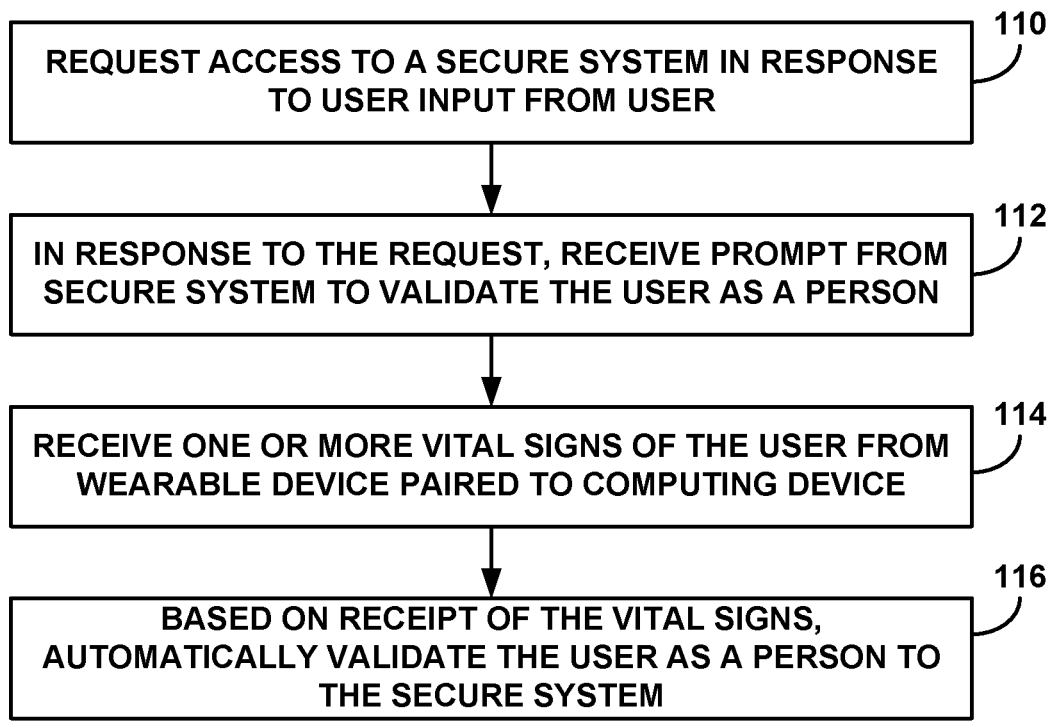
FIG. 5 is a flowchart illustrating an example operation of a computing device using a paired wearable device to automatically validate a user for access to a secure system, in accordance with the techniques of this disclosure.

FIG. 5 is a flowchart illustrating an example operation of a computing device using a paired wearable device to automatically validate a user for access to a secure system, in accordance with the techniques of this disclosure. The example operation of FIG. 5 is described with respect to computing device 28 from FIG. 2 and wearable device 58 from FIG. 3. In other examples, as described above, wearable device 58 may communicate directly with a secure system to automatically validate a user without need for a separate computing device.

Computing device 28 may execute a browser or another application through which a user may request to access a secure system, e.g., secure system 16 from FIG. 1, such as a shopping application or a retailer's website with an online payment portal. Computing device 28, in turn, requests access to the secure system in response to the user input (110).

In response to the access request, computing device 28 receives a prompt from the secure system to validate the user as a person and not a robot (112). The prompt may comprise a CAPTCHA request from the secure system via the web browser or other application executed on computing device 28. In some examples, the prompt may include two options for user validation, i.e., automatic validation or manual validation based on user input. In this example, upon receiving the prompt from the secure system, computing device 28 may present the prompt to the user, e.g., as a GUI or other user interface, and receive a selection of one of the two user validation options from the user. In the case where the user selects the manual validation option, the user may manually type characters or manually select an image via computing device 28 to respond to the prompt. In the case where the user selects the automatic validation option, user validation unit 46 of computing device 28 automatically validates the user as a person to the secure system as described in the following steps illustrated in FIG. 5.

Computing device 28 receives one or more vital signs of the user from a wearable computing device, e.g., wearable device 58 from FIG. 3, that is paired to computing device 28 (114). In one example, the one or more vital signs of the user may be monitored by wearable device 58 exclusively for user validation to the secure system. In this example, in response to the prompt from the secure system, user validation unit 46 may activate an interface of computing device 28 to communicate with wearable device 58, request the one or more vital signs of the user from wearable device 58, and, receive the one or more vital signs of the user from wearable device 58 via the interface.

In another example, the one or more vital signs of the user may be monitored by wearable device 58 for another application executed on computing device 28 that is unrelated to user validation to the secure system. For example, wearable device 58 may monitor the one or more vital signs for a health or fitness tracking application executed on computing device 28. In this example, the other application on computing device 28 may be continuously receiving the one or more vital signs of the user from wearable device 58. In response to the prompt from the secure system, user validation unit 46 may retrieve the one or more vital signs of the user from the other application.

Based on the receipt of the one or more vital signs of the user, user validation unit 46 of computing device 28 automatically validates the user as a person to the secure system (116). For example, to automatically validate the user as a person to the secure system, user validation unit 46 may first confirm that wearable device 58 is paired to computing device 28, and then confirm that the one or more vital signs of the user are being received from paired wearable device 58. As discussed in more detail above, the active receipt of any vital signs from paired wearable device 58 may be enough to validate that the user is a person and not a robot. In other words, the received vital signs may not be used to authenticate the identity of the user as a specific person, but instead are used to determine that the current user is a living person.

In the case where computing device 28 is not paired to wearable device 58 and/or is not receiving the one or more vital signs of the user from wearable device 58, user validation unit 46 may send a notification to the user of computing device 28, e.g., as an email, a text message, or a push notification, indicating that the user cannot be automatically validated as a person to the secure system. In addition, user validation unit 46 may send a request to the user for user input, e.g., manually typed characters or a manually selected image, to manually validate the user as a person to the secure system.

As described in more detail above with respect to FIGS. 1 and 3, in some examples, wearable device 58 may communicate directly with a secure system to automatically validate a user without need for a separate computing device. For example, wearable device 58 includes sensors 64 configured to monitor the one or more vital signs of the user. In this way, to automatically validate the user as a person to the secure system, wearable device 58 may confirm that the one or more vital signs of the user are being received directly from sensors 64.

In some examples, once the user is validated as a person to the secure system, computing device 28 establishes a session providing the user with access to the secure system, and user validation unit 46 may continuously monitor received vital signs during the session to ensure that a person, or in some cases the same person, is accessing the secure system over the entire session. For example, user validation unit 46 may continuously receive the one or more vital signs of the user during the session, and determine whether any of the received vital signs have changed during the session by at least a threshold amount. In one example, wearable device unit 44 of computing device 28 may store real-time, discrete sets of the continuously received vital signs in user profile 54 for the user. In this example, user validation unit 46 may compare a current set of vital signs received during the session against a previous set of vital signs received during the session and stored in user profile 54, and determine whether an amount of change between the current set of vital signs and the previous set of vital signs is greater than or equal to the threshold amount. Based on the determination that the vital signs have changed during the session by at least the threshold amount, user validation unit 46 may cancel the session with the secure system.

In some cases, user validation unit 46 may detect a sudden disappearance or disruption in the user's vital signs during the session with the secure system, which may indicate that the paired wearable device was detached from the user. In this case, user validation unit 46 may cancel the session with the secure system. In other cases, user validation unit 46 may detect the disruption in the user's vital signs followed by a reappearance of a different set of vital signs during the session, which may indicate that the paired wearable device was detached from the user and then attached to an unauthorized user. In this case, user validation unit 46 may again cancel the session with the secure system, and the user will need to re-validate or re-authenticate to re-gain access to the secure system.

Figure 6:
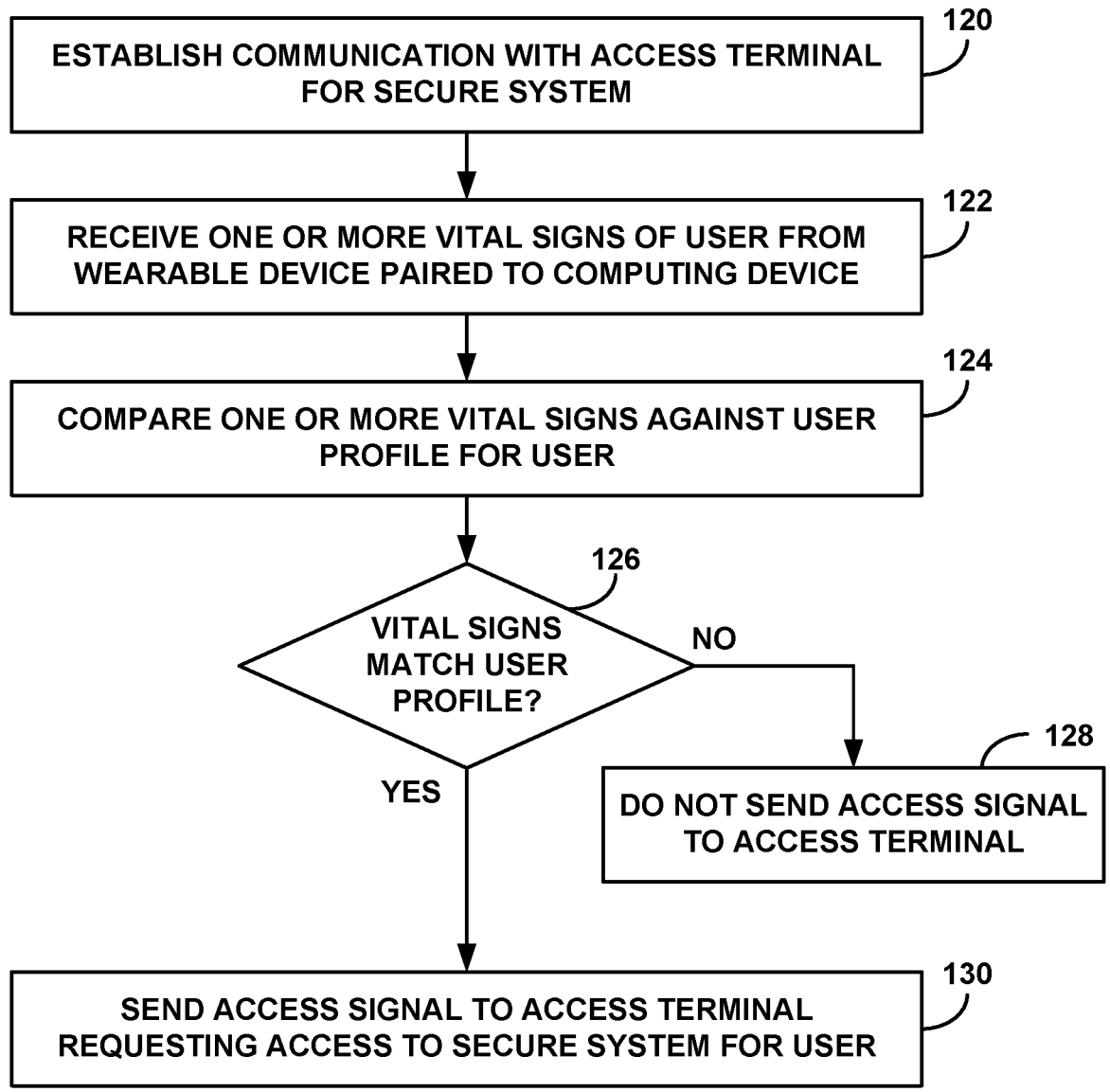
FIG. 6 is a flowchart illustrating an example operation of a computing device as a secure access badge using a paired wearable device to request access to a secure system, in accordance with the techniques of this disclosure.

FIG. 6 is a flowchart illustrating an example operation of a computing device as a secure access badge using a paired wearable device to request access to a secure system, in accordance with the techniques of this disclosure. The example operation of FIG. 6 is described with respect to computing device 28 from FIG. 2 operating as a secure access badge based on vital signs received from wearable device 58 from FIG. 3. In other examples, as described above, wearable device 58 itself may operate as a secure access badge and communicate directly with a secure system to gain access to the secure system for the user without need for a separate computing device.

Computing device 28 may execute an application to operate as a digital or virtual secure access badge for a user of computing device 28 to gain access to a secure building, a secure area of a building, a secure computing system, or a secure database within a computing system. Secure access unit 47 of computing device 28 first establishes communication with an access terminal for a secure system, e.g., access terminal 17 of secure system 16 from FIG. 1 (120). As described above, in one example, the access terminal may be a physical security checkpoint at the entrance of a secure location or at a computer terminal used to access a secure computing system. In this example, secure access unit 47 may detect the geolocation of computing device 28 and begin communicating with the access terminal via a short-range wireless communication protocol when within a certain distance. In another example, the access terminal may be a virtual security checkpoint at a login to a secure computing system or a secure database. In this example, secure access unit 47 may begin communicating with the access terminal via a network communication protocol based on a user input request.

Computing device 28 receives one or more vital signs of the user from a wearable computing device, e.g., wearable device 58 from FIG. 3, that is paired to computing device 28 (122). In one example, the one or more vital signs of the user may be monitored by wearable device 58 exclusively for user access to the secure system. In this example, in response to establishing communication with the secure system, secure access unit 47 may activate an interface of computing device 28 to communicate with wearable device 58, request the one or more vital signs of the user from wearable device 58, and, receive the one or more vital signs of the user from wearable device 58 via the interface.

In another example, the one or more vital signs of the user may be monitored by wearable device 58 for another application executed on computing device 28 that is unrelated to user access to the secure system. For example, wearable device 58 may monitor the one or more vital signs for a health or fitness tracking application executed on computing device 28. In this example, the other application on computing device 28 may be continuously receiving the one or more vital signs of the user from wearable device 58. In response to establishing communication with the secure system, secure access unit 47 may retrieve the one or more vital signs of the user from the other application.

Based on the receipt of the one or more vital signs of the user, secure access unit 47 compares the one or more vital signs of the user against a user profile 54 for the user stored by the computing device (124). In one example, user profile 54 stored on computing device 28 may comprise a real-time profile that includes a discrete set of the user's vital signs at a given point in time. In this example, secure access unit 47 may compare a current set of vital signs against a previous set of vital signs included in user profile 54. In another example, user profile 54 may comprise a historic profile that tracks the user's vital signs over time. In this example, secure access unit 47 may compare the current set of vital signs against the historic profile of vital signs included in user profile 54.

In the case where the one or more vital signs substantially match user profile 54 (YES branch of 126), secure access unit 47 sends the access signal to the access terminal requesting access to the secure system for the user (130). Once the access terminal authenticates the user based on the access signal, secure access unit 47 establishes a session providing the user with access to the secure system.

In the case where the one or more vital signs do not match user profile 54 (NO branch of 126), secure access unit 47 does not send the access signal to the access terminal for the secure system (128). In this case, secure access unit 47 may instead send a signal to the access terminal requesting a visual check of the user of computing device 28. For example, a security officer of the secure system or a manager of the authorized user of computing device 28 may receive a prompt for a visual check to verify the identity of the user. The visual check may be performed in person or via a video conference or video chat application executed on computing device 28 and a computing device of the security officer or manager. In some examples, to assist the security officer or manager, the signal requesting the visual check may include an indication of the user's geolocation and/or an indication of a computer system last accessed by the user. In some cases, e.g., where the visual check cannot be performed, secure access unit 47 may send a denial of access signal to the access terminal requesting that access to the secure system be denied for the user.

As described in more detail above with respect to FIGS. 1 and 3, in some examples, wearable device 58 may communicate directly with a secure system to gain access to the secure system for a user without need for a separate computing device. For example, wearable device 58 includes sensors 64 configured to monitor the one or more vital signs of the user. In this way, to gain access to the secure system for the user, wearable device 58 may receive the one or more vital signs from sensors 64, and perform the above described comparison to determine whether to send the access signal requesting access to the secure system for the user.

In some examples, once the user is granted access to the secure system, computing device 28 establishes a session providing the user with access to the secure system, and secure access unit 47 may continuously monitor received vital signs during the session to ensure that the same authorized user is accessing the secure system over the entire session. For example, secure access unit 47 may continuously receive the one or more vital signs of the user during the session, and determine whether any of the received vital signs have changed during the session by at least a threshold amount. Based on the determination that the vital signs have changed during the session by at least the threshold amount, secure access unit 47 may send a denial of access signal to the access terminal requesting that access to the secure system be denied or revoked for the user. Secure access unit 47 may send similar signals to the access terminal upon detection of a sudden disappearance or disruption in the user's vital signs and/or a reappearance of a different set of vital signs during the session.

Figure 7:
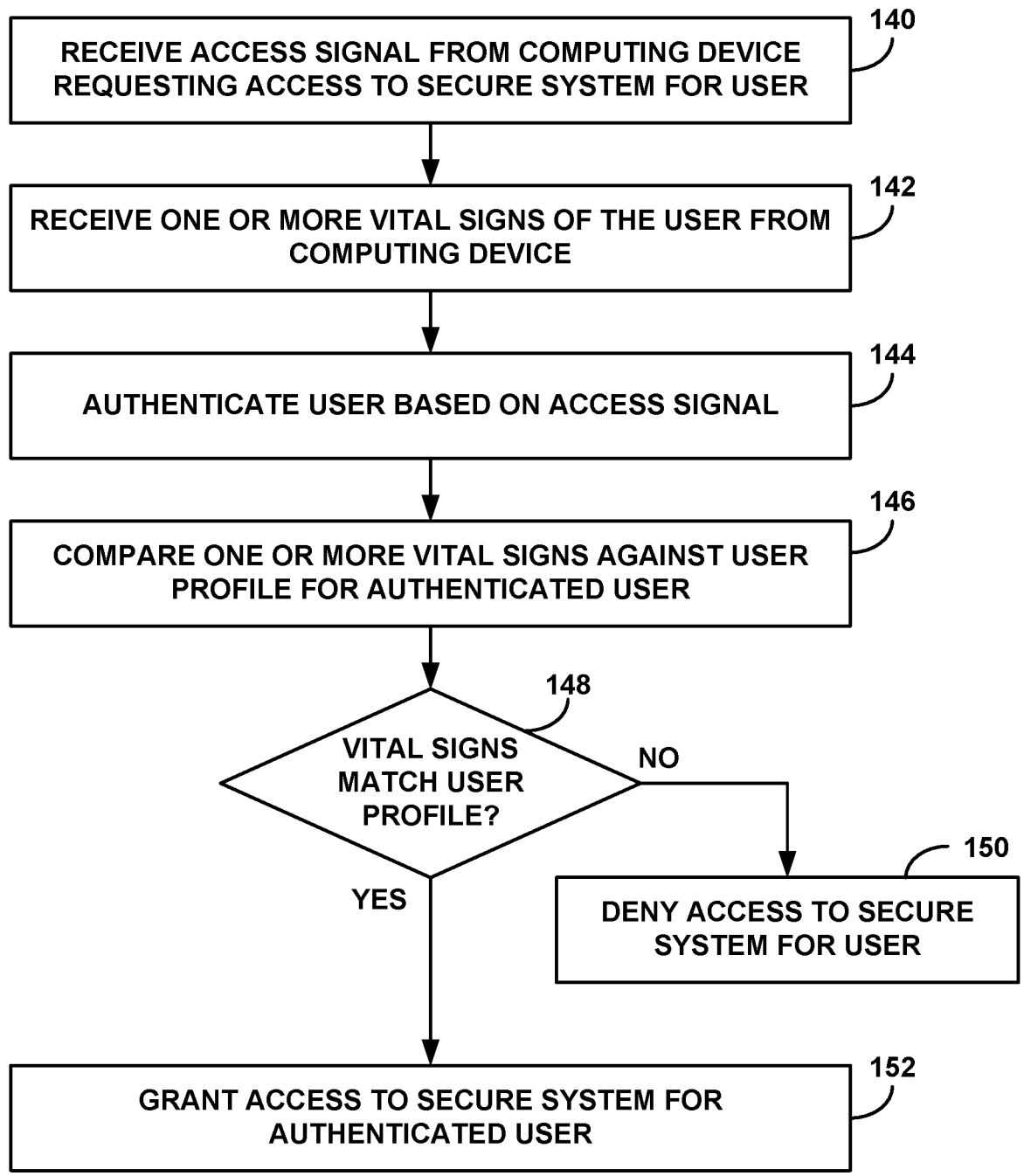
FIG. 7 is a flowchart illustrating an example operation of an access terminal for a secure system authenticating a user of a computing device for access to the secure system, in accordance with the techniques of this disclosure.

FIG. 7 is a flowchart illustrating an example operation of an access terminal for a secure system authenticating a user of a computing device for access to the secure system, in accordance with the techniques of this disclosure. The example operation of FIG. 7 is described with respect to access terminal 80 from FIG. 4 operating as a security checkpoint in connection with computing device 28 from FIG. 2 operating as a secure access bade based on vital signs received from wearable device 58 from FIG. 3. In other examples, as described above, access terminal 80 may communicate directly with wearable device 58 operating as a secure access badge without need for a separate computing device.

Access terminal 80 for a secure system, such as secure system 16 from FIG. 1, may receive an access signal from computing device 28 requesting access to the secure system for a user of computing device 28 (140). In one example, access terminal 80 may be a physical security checkpoint at the entrance of a secure building or a secure area within a building, or at a computer terminal used to access a secure computing system. In this example, access terminal 80 may receive communication, including the access signal, from computing device 28 when within a certain distance via a short-range wireless communication protocol. In another example, access terminal 80 may be a virtual security checkpoint at a login to a secure computing system or a secure database within a computing system. In this example, access terminal 80 may receive communication, including the access signal, from computing device 28 via a network communication protocol based on a user input request.

Access terminal 80 receives one or more vital signs of the user from computing device 28 (142). As described above, computing device 28 may be paired to wearable device 58, and may receive the vital signs of the user from paired wearable device 58 either exclusively for user access to the secure system or for another application executed on computing device 28 that is unrelated to user access to the secure system. As described in more detail above with respect to FIGS. 1 and 3, in some examples, access terminal 80 may receive the one or more vital signs of the user directly from wearable device 58 to grant access to the secure system for a user without need for a separate computing device.

Access signal authentication unit 96 of access terminal 80 authenticates the user based on the access signal received from computing device 28 (144). For example, access signal authentication unit 96 may compare the received access signal against a plurality of authorized access signals 102 stored in authorized user database 100 at access terminal 80, and authenticate the user of computing device 28 based on the received access signal matching one of authorized access signals 102. Although not shown in FIG. 7, in some examples, if the user cannot be authenticated based on the access signal, access terminal 80 may immediately deny access to the secure system for the user (150) without analyzing the received vital signs of the user.

Vital sign authentication unit 98 of access terminal 80 compares the one or more vital signs of the user against one of user profiles 104 for the authenticated user stored in authorized user database 100 at access terminal 80 (146). In one example, user profiles 104 stored in authorized user database 100 at access terminal 80 may comprise real-time profiles for different users that each includes a discrete set of the respective user's vital signs at a given point in time. In this example, vital sign authentication unit 98 may compare a current set of vital signs of the user against a previous set of vital signs included in the one of user profiles 104 for the authenticated user. In another example, user profiles 104 may comprise historic profiles that each tracks a respective user's vital signs over time. In this example, vital sign authentication unit 98 may compare the current set of vital signs of the user against the historic profile of vital signs included in the one of user profiles 104 for the authenticated user.

In the case where the one or more vital signs substantially match the one of user profiles 104 (YES branch of 148), authentication unit 94 of access terminal 80 grants access to the secure system for the authenticated user (152). In the case where the one or more vital signs do not match the one of user profiles 104 (NO branch of 148), authentication unit 94 denies access to the secure system for the authenticated user (150). In this case, authentication unit 94 may also initiate a visual check of the authenticated user of computing device 28. For example, a security officer of the secure system or a manager of the authorized user of computing device 28 may receive a prompt for a visual check to verify the identity of the denied user. The visual check may be performed in person or via a video conference or video chat application executed on computing device 28 and a computing device of the security officer or manager. In some examples, to assist the security officer or manager, authentication unit 94 may also determine the denied user's geo-location and/or a computer system last accessed by the denied user. In cases where the user's identity is verified by the visual check, the security officer or manager may override access terminal 80 and manually grant access to the secure system for the authenticated user.

In some examples, upon granting access to the secure system for a session, vital sign authentication unit 98 may continuously monitor received vital signs during the session to ensure that the same authenticated user is accessing the secure system over the entire session. For example, vital sign authentication unit 98 may continuously receive the one or more vital signs of the user during the session, and determine whether any of the received vital signs have changed during the session by at least a threshold amount. Based on the determination that the vital signs have changed during the session by at least the threshold amount, authentication unit 94 may deny or revoke access to the secure system for the authenticated user.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over a computer-readable medium as one or more instructions or code, and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry, as well as any combination of such components.

Accordingly, the term "processor," as used herein may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device or wireless handset, a mobile computing device, a wearable computing device, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A computing device comprising:
   a memory configured to store at least one user profile for a user of the computing device; and
   one or more processors in communication with the memory and configured to:
      establish communication using a short-range wireless communication protocol with an access terminal for a secure system;
      receive one or more vital signs of the user;
      compare the one or more vital signs of the user against the at least one user profile for the user;
      based on the one or more vital signs substantially matching the at least one user profile, send, to the access terminal, an access signal requesting access to the secure system for the user, wherein the one or more vital signs substantially match the at least one user profile when the comparison indicates that one or more vital signs have not changed at least a threshold amount relative to the at least one user profile;
      and
      in response to receiving access to the secure system for a user session:
         continuously monitor the one or more vital signs of the user during the user session, and
         based on the one or more vital signs of the user changing during the user session by at least the threshold amount or the one or more vital signs of the user disappearing, send a denial of access signal to the access terminal, wherein the denial of access signal includes an indication of a computing system being accessed by the user and a request to lock down the computing system.

2. The computing device of claim 1, wherein the computing device comprises a mobile device, and wherein the one or more processors are configured to receive the one or more vital signs of the user from a wearable device that is paired to the mobile device.

3. The computing device of claim 2, wherein, to receive the one or more vital signs of the user from the wearable device, the one or more processors are configured to:
   activate an interface of the mobile device to communicate with the wearable device;
   request the one or more vital signs from the wearable device; and
   in response to the request, receive the one or more vital signs from the wearable device via the interface.

4. The computing device of claim 2, wherein, to receive the one or more vital signs of the user from the wearable device, the one or more processors are configured to:
   continuously receive the one or more vital signs from the wearable device for an application executed by the one or more processors, wherein the application is unrelated to requesting access to the secure system; and
   retrieve the one or more vital signs from the application.

5. The computing device of claim 1, wherein the computing device comprises a wearable computing device including one or more sensors configured to monitor the one or more vital signs of the user, and wherein the one or more processors are configured to receive the one or more vital signs from the one or more sensors.

6. The computing device of claim 1, wherein, to compare the one or more vital signs against the at least one user profile, the one or more processors are configured to one of:
   compare a current set of vital signs against a previous discrete set of vital signs of the user included in the at least one user profile; or
   compare the current set of vital signs against a historic profile of the one or more vital signs of the user included in the at least one user profile.

7. The computing device of claim 1, wherein the denial of access signal includes a request that access to the secure system be revoked for the user.

8. The computing device of claim 1, wherein the denial of access signal includes a request for a visual check of the user.

9. A method comprising:
   establishing, by a computing device, communication using a short-range wireless communication protocol with an access terminal for a secure system;
   receiving, by the computing device, one or more vital signs of a user of the computing device;
   comparing, by the computing device, the one or more vital signs of the user against at least one user profile for the user stored by the computing device;
   based on the one or more vital signs substantially matching the at least one user profile, sending, by the computing device and to the access terminal, an access signal requesting access to the secure system for the user, wherein the one or more vital signs substantially match the at least one user profile when the comparison indicates that one or more vital signs have not changed by at least a threshold amount relative to the at least one user profile; and
   in response to receiving access to the secure system for a user session:
      continuously monitoring the one or more vital signs of the user during the user session; and
      based on the one or more vital signs of the user changing during the user session by at least the threshold amount or the one or more vital signs of the user disappearing, sending a denial of access signal to the access terminal, wherein the denial of access signal includes an indication of a computing system being accessed by the user and a request to lock down the computing system.

10. The method of claim 9, wherein the computing device is a mobile device, and wherein receiving the one or more vital signs of the user comprises receiving the one or more vital signs from a wearable device that is paired to the mobile device.

11. The method of claim 10, wherein receiving the one or more vital signs from the wearable device comprises:
   activating an interface of the mobile device to communicate with the wearable device;
   requesting the one or more vital signs from the wearable device; and
   in response to the request, receiving the one or more vital signs from the wearable device via the interface.

12. The method of claim 10, wherein receiving the one or more vital signs from the wearable device comprises:
   continuously receiving the one or more vital signs from the wearable device for an application executed by on the mobile device, wherein the application is unrelated to requesting access to the secure system; and
   retrieving the one or more vital signs from the application.

13. The method of claim 9, wherein the computing device comprises a wearable computing device including one or more sensors configured to monitor the one or more vital signs of the user, and wherein receiving the one or more vital signs of the user comprises receiving the one or more vital signs from the one or more sensors.

14. The method of claim 9, wherein comparing the one or more vital signs against the at least one user profile comprises one of:
   comparing a current set of vital signs against a previous discrete set of vital signs of the user included in the at least one user profile; or
   comparing the current set of vital signs against a historic profile of the one or more vital signs of the user included in the at least one user profile.

15. The method of claim 9, wherein the denial of access signal includes a request that access to the secure system be revoked for the user.

16. The method of claim 9, wherein the denial of access signal includes a request for a visual check of the user.

17. A wearable device comprising:
   a memory configured to store at least one user profile for a user of the wearable device;
   one or more sensors configured to monitor one or more vital signs from the user; and
   one or more processors in communication with the memory and the one or more sensors, the one or more processors configured to:
      establish communication using a short-range wireless communication protocol with an access terminal for a secure system;
      receive the one or more vital signs from the one or more sensors;
      compare the one or more vital signs of the user against the at least one user profile for the user;
      based on the one or more vital signs substantially matching the at least one user profile, send, to the access terminal, an access signal requesting access to the secure system for the user, wherein the one or more vital signs substantially match the at least one user profile when the comparison indicates that one or more vital signs have not changed by at least a threshold amount relative to the at least one user profile;
      and
      in response to receiving access to the secure system for a user session:
         continuously monitor the one or more vital signs of the user during the user session, and
         based on one or more vital signs of the user changing during the user session by at least the threshold amount or the one or more vital signs of the user disappearing, send a denial of access signal to the access terminal, wherein the denial of access signal includes an indication of a computing system being accessed by the user and a request to lock down the computing system.

18. The wearable device of claim 17, wherein, to compare the one or more vital signs against the at least one user profile, the one or more processors are configured to one of:
   compare a current set of vital signs against a previous discrete set of vital signs of the user included in the at least one user profile; or
   compare the current set of vital signs against a historic profile of the one or more vital signs of the user included in the at least one user profile.

19. The wearable device of claim 17, wherein the denial of access signal includes a request that access to the secure system be revoked for the user.

20. The wearable device of claim 17, wherein the denial of access signal includes a request for a visual check of the user.

* * * * *